(12) United States Patent
Tremblay

(10) Patent No.: US 8,715,250 B2
(45) Date of Patent: May 6, 2014

(54) SAFETY CATHETER AND NEEDLE ASSEMBLY

(75) Inventor: Kathleen Tremblay, Westfield, MA (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/616,464

(22) Filed: Sep. 14, 2012

(65) Prior Publication Data
US 2013/0245567 A1    Sep. 19, 2013

Related U.S. Application Data

(60) Provisional application No. 61/539,153, filed on Sep. 26, 2011.

(51) Int. Cl.
*A61M 5/00* (2006.01)

(52) U.S. Cl.
USPC .......................................................... 604/263

(58) Field of Classification Search
USPC ................. 604/162, 164.08, 192, 198, 263
See application file for complete search history.

(56) References Cited

U.S. PATENT DOCUMENTS

| | | | |
|---|---|---|---|
| 3,134,380 A | 5/1964 | Armao |
| 3,884,230 A | 5/1975 | Wulff |
| 4,387,879 A | 6/1983 | Tauschinski |
| 4,512,766 A | 4/1985 | Vailancourt |
| 4,725,267 A | 2/1988 | Vaillancourt |
| 4,755,170 A | 7/1988 | Golden |
| 4,778,453 A | 10/1988 | Lopez |
| 4,795,432 A | 1/1989 | Karczmer |
| 4,804,370 A | 2/1989 | Haber |
| 4,804,371 A | 2/1989 | Vaillancourt |
| 4,808,169 A | 2/1989 | Haber |
| 4,834,718 A | 5/1989 | Mcdonald |
| 4,842,591 A | 6/1989 | Luther |
| 4,846,805 A | 7/1989 | Sitar |
| 4,850,977 A | 7/1989 | Bayless |
| 4,850,994 A | 7/1989 | Zerbst |
| 4,863,434 A | 9/1989 | Bayless |
| 4,863,436 A | 9/1989 | Glick |
| 4,867,746 A | 9/1989 | Dufresne |
| 4,874,377 A | 10/1989 | Newgard |
| 4,908,022 A | 3/1990 | Haber |

(Continued)

FOREIGN PATENT DOCUMENTS

| WO | WO 2010/061405 | 6/2010 |
|---|---|---|
| WO | WO 2011/036574 | 3/2011 |
| WO | WO 2011/154767 | 12/2011 |
| WO | WO 2012/014018 | 2/2012 |

OTHER PUBLICATIONS

U.S. Appl. No. 13/616,464, filed Sep. 14, 2012, Tremblay.
U.S. Appl. No. 13/625,947, filed Sep. 25, 2012, Finnestad et al.

(Continued)

*Primary Examiner* — Jason Flick
*Assistant Examiner* — Diva K Chander
(74) *Attorney, Agent, or Firm* — Lisa E. Winsor, Esq.

(57) ABSTRACT

An intravenous catheter and safety needle assembly is disclosed which includes a catheter assembly, a needle assembly and a needle guard. The needle guard is supported within a hub of the catheter and is positioned to engage an enlarged diameter portion of a needle of the needle assembly during withdrawal of the needle from the catheter assembly to effect an inversion of the needle guard about a sharpened tip of the needle.

17 Claims, 5 Drawing Sheets

(56) References Cited

U.S. PATENT DOCUMENTS

| | | |
|---|---|---|
| 4,909,794 A | 3/1990 | Haber |
| 4,911,706 A | 3/1990 | Levitt |
| 4,917,668 A | 4/1990 | Haindl |
| 4,921,486 A | 5/1990 | De chellis |
| 4,921,490 A | 5/1990 | Spier |
| 4,927,415 A | 5/1990 | Brodsky |
| 4,929,241 A | 5/1990 | Kulli |
| 4,931,040 A | 6/1990 | Haber |
| 4,935,010 A | 6/1990 | Cox |
| 4,944,723 A | 7/1990 | Haber |
| 4,944,728 A | 7/1990 | Carrell |
| 4,952,207 A | 8/1990 | Lemieux |
| 4,955,866 A | 9/1990 | Corey |
| 4,964,854 A | 10/1990 | Luther |
| 4,978,343 A | 12/1990 | Dysarz |
| 4,978,344 A | 12/1990 | Dombrowski |
| 4,986,813 A | 1/1991 | Blake, III |
| 4,986,819 A | 1/1991 | Sobel |
| 4,994,041 A | 2/1991 | Dombrowski |
| 4,994,046 A | 2/1991 | Wesson |
| 4,998,922 A | 3/1991 | Kuracina |
| 5,002,533 A | 3/1991 | Jullien |
| 5,013,305 A | 5/1991 | Opie |
| 5,015,234 A | 5/1991 | Jullien |
| 5,015,240 A | 5/1991 | Soproni |
| 5,015,241 A | 5/1991 | Feimer |
| 5,015,242 A | 5/1991 | Heifetz |
| 5,030,208 A | 7/1991 | Novacek |
| 5,049,136 A | 9/1991 | Johnson |
| 5,051,109 A | 9/1991 | Simon |
| 5,053,014 A | 10/1991 | Van heugten |
| 5,053,017 A | 10/1991 | Chamuel |
| 5,059,180 A | 10/1991 | Mclees |
| 5,059,184 A | 10/1991 | Dyke |
| 5,080,651 A | 1/1992 | Julien |
| 5,084,018 A | 1/1992 | Tsao |
| 5,085,648 A | 2/1992 | Purdy |
| 5,092,461 A | 3/1992 | Adam |
| 5,092,851 A | 3/1992 | Ragner |
| 5,104,378 A | 4/1992 | Haber |
| 5,112,311 A | 5/1992 | Utterberg |
| 5,114,404 A | 5/1992 | Paxton |
| 5,120,321 A | 6/1992 | Oksman |
| 5,122,118 A | 6/1992 | Haber |
| 5,122,124 A | 6/1992 | Novacek |
| 5,127,905 A | 7/1992 | Lemieux |
| 5,131,405 A | 7/1992 | Burns |
| 5,135,504 A | 8/1992 | Mclees |
| 5,137,515 A | 8/1992 | Hogan |
| 5,147,327 A | 9/1992 | Johnson |
| 5,154,699 A | 10/1992 | Ryan |
| 5,154,703 A | 10/1992 | Bonaldo |
| 5,156,596 A | 10/1992 | Balbierz |
| 5,158,554 A | 10/1992 | Jepson |
| 5,169,391 A | 12/1992 | Vogel |
| 5,171,229 A | 12/1992 | Mcneil |
| 5,171,300 A | 12/1992 | Blake, III |
| 5,176,650 A | 1/1993 | Haining |
| 5,176,655 A | 1/1993 | Mccormick |
| 5,176,656 A | 1/1993 | Bayless |
| 5,180,369 A | 1/1993 | Dysarz |
| 5,180,370 A | 1/1993 | Gillespie |
| 5,183,468 A | 2/1993 | Mclees |
| 5,188,607 A | 2/1993 | Wu |
| 5,195,723 A | 3/1993 | Schauerte |
| 5,195,974 A | 3/1993 | Hardy |
| 5,195,980 A | 3/1993 | Catlin |
| 5,199,947 A | 4/1993 | Lopez |
| 5,205,827 A | 4/1993 | Novacek |
| 5,205,829 A | 4/1993 | Lituchy |
| 5,207,656 A | 5/1993 | Kranys |
| 5,211,629 A | 5/1993 | Pressly |
| 5,211,633 A | 5/1993 | Stouder, Jr. |
| 5,215,525 A | 6/1993 | Sturman |
| 5,215,528 A | 6/1993 | Purdy |
| 5,215,533 A | 6/1993 | Robb |
| 5,215,534 A | 6/1993 | De harde |
| 5,215,538 A | 6/1993 | Larkin |
| 5,222,505 A | 6/1993 | Burns |
| 5,224,936 A | 7/1993 | Gallagher |
| 5,228,646 A | 7/1993 | Raines |
| 5,232,456 A | 8/1993 | Gonzalez |
| 5,232,458 A | 8/1993 | Chen |
| 5,234,410 A | 8/1993 | Graham |
| 5,242,393 A | 9/1993 | Brimball |
| 5,242,400 A | 9/1993 | Blake, III |
| 5,242,402 A | 9/1993 | Chen |
| 5,242,411 A | 9/1993 | Yamamoto |
| 5,246,427 A | 9/1993 | Sturman |
| RE34,416 E | 10/1993 | Lemieux |
| 5,251,873 A | 10/1993 | Atkinson |
| 5,254,099 A | 10/1993 | Kuracina |
| 5,256,152 A | 10/1993 | Marks |
| 5,261,880 A | 11/1993 | Streck |
| 5,261,894 A | 11/1993 | Smith |
| 5,263,933 A | 11/1993 | Novacek |
| 5,266,072 A | 11/1993 | Utterberg |
| 5,267,966 A | 12/1993 | Paul |
| 5,267,976 A | 12/1993 | Guerineau |
| 5,269,763 A | 12/1993 | Boehmer |
| 5,269,764 A | 12/1993 | Vetter |
| 5,269,765 A | 12/1993 | Kuracina |
| 5,269,771 A | 12/1993 | Thomas |
| 5,273,540 A | 12/1993 | Luther |
| 5,277,342 A | 1/1994 | Dickau |
| 5,279,570 A | 1/1994 | Dombrowski |
| 5,279,571 A | 1/1994 | Larkin |
| 5,279,591 A | 1/1994 | Simon |
| 5,290,246 A | 3/1994 | Yamamoto |
| 5,293,970 A | 3/1994 | Schneider |
| 5,295,657 A | 3/1994 | Atkinson |
| 5,295,658 A | 3/1994 | Atkinson |
| 5,295,963 A | 3/1994 | Deeks |
| 5,295,972 A | 3/1994 | Mischenko |
| 5,297,777 A | 3/1994 | Yie |
| 5,300,032 A | 4/1994 | Hibbs |
| 5,300,033 A | 4/1994 | Miller |
| 5,300,034 A | 4/1994 | Behnke |
| 5,300,035 A | 4/1994 | Clement |
| 5,300,040 A | 4/1994 | Martin |
| 5,300,045 A | 4/1994 | Plassche, Jr. |
| 5,304,136 A | 4/1994 | Erskine |
| 5,304,151 A | 4/1994 | Kuracina |
| 5,304,156 A | 4/1994 | Sylvanowicz |
| 5,306,243 A | 4/1994 | Bonaldo |
| 5,308,336 A | 5/1994 | Hart |
| 5,312,355 A | 5/1994 | Lee |
| 5,312,362 A | 5/1994 | Pfolsgraf |
| 5,312,363 A | 5/1994 | Ryan |
| 5,312,371 A | 5/1994 | Dombrowski |
| 5,312,372 A | 5/1994 | De harde |
| 5,322,517 A | 6/1994 | Sircom |
| 5,322,518 A | 6/1994 | Schneider |
| 5,324,271 A | 6/1994 | Abiuso |
| 5,328,478 A | 7/1994 | Mcvay |
| 5,328,482 A | 7/1994 | Sircom |
| 5,328,484 A | 7/1994 | Somers |
| 5,328,485 A | 7/1994 | Moreno |
| 5,330,435 A | 7/1994 | Vaillancourt |
| 5,330,437 A | 7/1994 | Durman |
| 5,334,158 A | 8/1994 | Mclees |
| 5,334,159 A | 8/1994 | Turkel |
| 5,336,192 A | 8/1994 | Palestrant |
| 5,336,198 A | 8/1994 | Silver |
| 5,336,199 A | 8/1994 | Castillo |
| 5,336,200 A | 8/1994 | Streck |
| 5,342,316 A | 8/1994 | Wallace |
| 5,342,319 A | 8/1994 | Watson |
| 5,344,161 A | 9/1994 | Sandgren |
| 5,344,408 A | 9/1994 | Partika |
| 5,344,414 A | 9/1994 | Lopez |
| 5,348,544 A | 9/1994 | Sweeney |
| 5,350,362 A | 9/1994 | Stouder, Jr. |
| 5,350,363 A | 9/1994 | Goode |

(56) References Cited

U.S. PATENT DOCUMENTS

| | | |
|---|---|---|
| 5,352,205 A | 10/1994 | Dales |
| 5,353,837 A | 10/1994 | Faust |
| 5,354,280 A | 10/1994 | Haber |
| 5,356,384 A | 10/1994 | Haber |
| 5,360,413 A | 11/1994 | Leason |
| 5,364,370 A | 11/1994 | Szerlip |
| 5,364,372 A | 11/1994 | Danks |
| 5,368,574 A | 11/1994 | Antonacci |
| 5,376,077 A | 12/1994 | Gomringer |
| 5,380,288 A | 1/1995 | Hart |
| 5,380,305 A | 1/1995 | Ghouri |
| 5,382,235 A | 1/1995 | Sak |
| 5,383,860 A | 1/1995 | Lau |
| 5,385,550 A | 1/1995 | Su |
| 5,389,081 A | 2/1995 | Castro |
| 5,390,898 A | 2/1995 | Smedley |
| 5,395,338 A | 3/1995 | Gaba |
| 5,395,346 A | 3/1995 | Maggioni |
| 5,395,347 A | 3/1995 | Blecher |
| 5,395,352 A | 3/1995 | Penny |
| 5,403,284 A | 4/1995 | Gross |
| 5,405,323 A | 4/1995 | Rogers |
| 5,405,327 A | 4/1995 | Chen |
| 5,405,331 A | 4/1995 | Behnke |
| 5,409,461 A | 4/1995 | Steinman |
| 5,409,464 A | 4/1995 | Villalobos |
| 5,411,486 A | 5/1995 | Zadini |
| 5,411,492 A | 5/1995 | Sturman |
| 5,415,638 A | 5/1995 | Novacek |
| 5,417,659 A | 5/1995 | Gaba |
| 5,417,673 A | 5/1995 | Gordon |
| 5,419,766 A | 5/1995 | Chang |
| 5,423,766 A | 6/1995 | Cesare |
| 5,425,718 A | 6/1995 | Tay |
| 5,425,720 A | 6/1995 | Rogalsky |
| 5,429,596 A | 7/1995 | Arias |
| 5,429,619 A | 7/1995 | Furnish |
| 5,431,631 A | 7/1995 | Lu |
| 5,431,632 A | 7/1995 | Lu |
| 5,433,703 A | 7/1995 | Utterberg |
| 5,437,646 A | 8/1995 | Hunt |
| 5,439,451 A | 8/1995 | Collinson |
| 5,441,487 A | 8/1995 | Vedder |
| 5,443,452 A | 8/1995 | Hart |
| 5,443,454 A | 8/1995 | Tanabe |
| 5,447,501 A | 9/1995 | Karlsson |
| 5,453,095 A | 9/1995 | Davila |
| 5,454,790 A | 10/1995 | Dubrul |
| 5,456,284 A | 10/1995 | Ryan |
| 5,456,675 A | 10/1995 | Wolbring |
| 5,458,640 A | 10/1995 | Gerrone |
| 5,458,658 A | 10/1995 | Sircom |
| 5,460,603 A | 10/1995 | Desantis |
| 5,462,531 A | 10/1995 | Novacek |
| 5,465,938 A | 11/1995 | Werge |
| 5,466,223 A | 11/1995 | Bressler |
| 5,466,230 A | 11/1995 | Davila |
| 5,470,319 A | 11/1995 | Mayer |
| 5,472,418 A | 12/1995 | Palestrant |
| 5,474,544 A | 12/1995 | Lynn |
| 5,478,313 A | 12/1995 | White |
| 5,480,393 A | 1/1996 | Bommarito |
| 5,484,401 A | 1/1996 | Rodriguez |
| 5,486,190 A | 1/1996 | Green |
| 5,487,728 A | 1/1996 | Vaillancourt |
| 5,487,733 A | 1/1996 | Caizza |
| 5,487,850 A | 1/1996 | Vanderploeg |
| 5,489,274 A | 2/1996 | Chu |
| 5,492,147 A | 2/1996 | Challender |
| 5,492,304 A | 2/1996 | Smith |
| 5,496,274 A | 3/1996 | Graves |
| 5,496,280 A | 3/1996 | Vandenbroek |
| 5,501,426 A | 3/1996 | Atkinson |
| 5,501,670 A | 3/1996 | Sak |
| 5,501,675 A | 3/1996 | Erskine |
| 5,507,732 A | 4/1996 | Mcclure |
| 5,509,433 A | 4/1996 | Paradis |
| 5,514,098 A | 5/1996 | Pfoslgraf |
| 5,514,116 A | 5/1996 | Vaillancourt |
| 5,514,117 A | 5/1996 | Lynn |
| 5,520,649 A | 5/1996 | Novacek |
| 5,520,655 A | 5/1996 | Davila |
| 5,520,666 A | 5/1996 | Choudhury |
| 5,531,701 A | 7/1996 | Luther |
| 5,533,974 A | 7/1996 | Gaba |
| 5,533,975 A | 7/1996 | Lu |
| 5,535,785 A | 7/1996 | Werge |
| 5,538,505 A | 7/1996 | Weinstein |
| 5,538,508 A | 7/1996 | Steyn |
| 5,540,661 A | 7/1996 | Tomisaka |
| 5,540,662 A | 7/1996 | Nicholson |
| 5,545,146 A | 8/1996 | Ishak |
| 5,545,152 A | 8/1996 | Funderburk |
| 5,549,565 A | 8/1996 | Ryan |
| 5,549,566 A | 8/1996 | Elias |
| 5,549,570 A | 8/1996 | Rogalsky |
| 5,549,576 A | 8/1996 | Patterson |
| 5,549,651 A | 8/1996 | Lynn |
| 5,554,131 A | 9/1996 | Lacivita |
| 5,558,651 A | 9/1996 | Crawford |
| 5,562,629 A | 10/1996 | Haughton |
| 5,562,630 A | 10/1996 | Nichols |
| 5,562,632 A | 10/1996 | Davila |
| 5,562,633 A | 10/1996 | Wozencroft |
| 5,562,636 A | 10/1996 | Utterberg |
| 5,562,637 A | 10/1996 | Utterberg |
| 5,569,202 A | 10/1996 | Kovalic |
| 5,569,203 A | 10/1996 | Chen |
| 5,569,205 A | 10/1996 | Hart |
| 5,569,209 A | 10/1996 | Roitman |
| 5,569,288 A | 10/1996 | Yoon |
| 5,573,545 A | 11/1996 | Yoon |
| 5,575,774 A | 11/1996 | Chen |
| 5,575,777 A | 11/1996 | Davidner |
| 5,575,804 A | 11/1996 | Yoon |
| 5,578,059 A | 11/1996 | Patzer |
| 5,582,594 A | 12/1996 | Chen |
| 5,582,597 A | 12/1996 | Brimhall |
| 5,584,808 A | 12/1996 | Healy |
| 5,584,809 A | 12/1996 | Gaba |
| 5,584,810 A | 12/1996 | Brimhall |
| 5,584,818 A | 12/1996 | Morrison |
| 5,584,848 A | 12/1996 | Yoon |
| 5,584,849 A | 12/1996 | Yoon |
| 5,584,850 A | 12/1996 | Hart |
| 5,588,966 A | 12/1996 | Atsumi |
| 5,591,134 A | 1/1997 | Shu |
| 5,591,137 A | 1/1997 | Stevens |
| 5,591,190 A | 1/1997 | Yoon |
| 5,591,193 A | 1/1997 | Yoon |
| 5,599,310 A | 2/1997 | Bogert |
| 5,601,532 A | 2/1997 | Gaba |
| 5,601,534 A | 2/1997 | Turner |
| 5,601,536 A | 2/1997 | Crawford |
| 5,607,396 A | 3/1997 | Yoon |
| 5,607,439 A | 3/1997 | Yoon |
| 5,611,781 A | 3/1997 | Sircom |
| 5,611,792 A | 3/1997 | Gustafsson |
| 5,613,500 A | 3/1997 | Bishop |
| 5,613,663 A | 3/1997 | Schmidt |
| 5,613,952 A | 3/1997 | Pressly, Sr. |
| 5,613,954 A | 3/1997 | Nelson |
| 5,613,956 A | 3/1997 | Patterson |
| 5,616,129 A | 4/1997 | Mayer |
| 5,616,130 A | 4/1997 | Mayer |
| 5,618,271 A | 4/1997 | Yoon |
| 5,630,803 A | 5/1997 | Tamaro |
| 5,634,913 A | 6/1997 | Stinger |
| 5,634,934 A | 6/1997 | Yoon |
| 5,643,227 A | 7/1997 | Stevens |
| 5,645,076 A | 7/1997 | Yoon |
| 5,645,533 A | 7/1997 | Blaeser |
| 5,651,772 A | 7/1997 | Arnett |
| 5,653,698 A | 8/1997 | Niedospial |

(56) References Cited

U.S. PATENT DOCUMENTS

| | | |
|---|---|---|
| 5,662,610 A | 9/1997 | Sircom |
| 5,669,891 A | 9/1997 | Vaillancourt |
| 5,672,160 A | 9/1997 | Osterlind |
| 5,672,161 A | 9/1997 | Allen |
| 5,676,681 A | 10/1997 | Yoon |
| 5,676,682 A | 10/1997 | Yoon |
| 5,676,683 A | 10/1997 | Yoon |
| 5,683,365 A | 11/1997 | Brown |
| 5,683,368 A | 11/1997 | Schmidt |
| 5,685,855 A | 11/1997 | Erskine |
| 5,685,860 A | 11/1997 | Chang |
| 5,688,240 A | 11/1997 | Novacek |
| 5,688,253 A | 11/1997 | Paradis |
| 5,688,254 A | 11/1997 | Lopez |
| 5,688,286 A | 11/1997 | Yoon |
| 5,693,025 A | 12/1997 | Stevens |
| 5,693,031 A | 12/1997 | Ryan |
| 5,695,474 A | 12/1997 | Daugherty |
| 5,696,466 A | 12/1997 | Li |
| 5,697,907 A | 12/1997 | Gaba |
| 5,699,821 A | 12/1997 | Paradis |
| 5,700,249 A | 12/1997 | Jenkins |
| 5,700,250 A | 12/1997 | Erskine |
| 5,702,367 A | 12/1997 | Cover |
| 5,709,664 A | 1/1998 | Vandenbroek |
| 5,718,688 A | 2/1998 | Wozencroft |
| 5,718,689 A | 2/1998 | Stevenson |
| 5,718,691 A | 2/1998 | Russo |
| 5,720,734 A | 2/1998 | Copenhaver |
| 5,722,958 A | 3/1998 | Gravener |
| 5,725,503 A | 3/1998 | Arnett |
| 5,735,827 A | 4/1998 | Adwers |
| 5,738,144 A | 4/1998 | Rogers |
| 5,738,665 A | 4/1998 | Caizza |
| 5,743,884 A | 4/1998 | Hasson |
| 5,743,888 A | 4/1998 | Wilkes |
| 5,743,891 A | 4/1998 | Tolkoff |
| 5,746,718 A | 5/1998 | Steyn |
| 5,749,857 A | 5/1998 | Cuppy |
| 5,749,859 A | 5/1998 | Powell |
| 5,749,861 A | 5/1998 | Guala |
| 5,749,889 A | 5/1998 | Bacich |
| 5,755,699 A | 5/1998 | Blecher |
| 5,755,701 A | 5/1998 | Sarstedt |
| 5,772,636 A | 6/1998 | Brimhall |
| 5,776,113 A | 7/1998 | Daugherty |
| 5,779,681 A | 7/1998 | Bonn |
| 5,779,684 A | 7/1998 | Tamaro |
| 5,782,804 A | 7/1998 | Mcmahon |
| D397,434 S | 8/1998 | Pike |
| 5,788,675 A | 8/1998 | Mayer |
| 5,792,121 A | 8/1998 | Tamaro |
| 5,795,339 A | 8/1998 | Erskine |
| 5,797,897 A | 8/1998 | Jepson |
| 5,800,403 A | 9/1998 | Pressly, Sr. |
| 5,803,919 A | 9/1998 | Hart |
| 5,806,831 A | 9/1998 | Paradis |
| 5,807,350 A | 9/1998 | Diaz |
| 5,807,352 A | 9/1998 | Tamaro |
| 5,807,353 A | 9/1998 | Schmitz |
| 5,810,784 A | 9/1998 | Tamaro |
| 5,814,018 A | 9/1998 | Elson |
| 5,817,069 A | 10/1998 | Arnett |
| 5,817,070 A | 10/1998 | Tamaro |
| 5,820,606 A | 10/1998 | Davis |
| 5,820,614 A | 10/1998 | Erskine |
| 5,820,621 A | 10/1998 | Yale |
| 5,830,189 A | 11/1998 | Chang |
| 5,833,670 A | 11/1998 | Dillon |
| 5,851,196 A | 12/1998 | Arnett |
| 5,853,393 A | 12/1998 | Bogert |
| 5,853,399 A | 12/1998 | Sasaki |
| 5,857,999 A | 1/1999 | Quick |
| 5,858,000 A | 1/1999 | Novacek |
| 5,858,007 A | 1/1999 | Fagan |
| 5,865,806 A | 2/1999 | Howell |
| 5,871,471 A | 2/1999 | Ryan |
| 5,879,331 A | 3/1999 | Osterlind |
| 5,879,337 A | 3/1999 | Kuracina |
| 5,882,337 A | 3/1999 | Bogert |
| 5,885,256 A | 3/1999 | Chern |
| 5,891,093 A | 4/1999 | Dysarz |
| 5,899,887 A | 5/1999 | Liu |
| 5,910,130 A | 6/1999 | Caizza |
| 5,911,705 A | 6/1999 | Howell |
| 5,911,710 A | 6/1999 | Barry |
| 5,916,198 A | 6/1999 | Dillow |
| 5,919,168 A | 7/1999 | Wheeler |
| 5,919,174 A | 7/1999 | Hanson |
| 5,925,020 A | 7/1999 | Nestell |
| 5,935,104 A | 8/1999 | Janek |
| 5,941,850 A | 8/1999 | Shah |
| 5,951,515 A | 9/1999 | Osterlind |
| 5,951,529 A | 9/1999 | Utterberg |
| 5,954,698 A | 9/1999 | Pike |
| 5,954,708 A | 9/1999 | Lopez |
| 5,957,887 A | 9/1999 | Osterlind |
| 5,957,898 A | 9/1999 | Jepson |
| 5,967,490 A | 10/1999 | Pike |
| 5,968,068 A | 10/1999 | Dehdashtian |
| 5,971,957 A | 10/1999 | Luther |
| 5,989,224 A | 11/1999 | Exline |
| 5,993,419 A | 11/1999 | Lo |
| 5,997,486 A | 12/1999 | Burek |
| 5,997,507 A | 12/1999 | Dysarz |
| 6,001,080 A | 12/1999 | Kuracina |
| 6,004,294 A | 12/1999 | Brimhall |
| 6,012,213 A | 1/2000 | Chang |
| 6,015,397 A | 1/2000 | Elson |
| 6,024,729 A | 2/2000 | Dehdashtian |
| 6,033,386 A | 3/2000 | Novacek |
| 6,036,672 A | 3/2000 | Allen |
| 6,039,302 A | 3/2000 | Cote, Sr. |
| 6,048,335 A | 4/2000 | Mayer |
| 6,053,861 A | 4/2000 | Grossi |
| 6,068,011 A | 5/2000 | Paradis |
| 6,074,370 A | 6/2000 | Pressly, Jr. |
| 6,077,244 A | 6/2000 | Botich |
| 6,079,432 A | 6/2000 | Paradis |
| 6,080,135 A | 6/2000 | Van Stokkum |
| 6,080,137 A | 6/2000 | Pike |
| 6,086,566 A | 7/2000 | Arnissolle |
| 6,099,500 A | 8/2000 | Dysarz |
| 6,099,505 A | 8/2000 | Ryan |
| 6,102,894 A | 8/2000 | Dysarz |
| RE36,885 E | 9/2000 | Blecher |
| 6,117,107 A | 9/2000 | Chen |
| 6,117,108 A | 9/2000 | Woehr |
| 6,117,110 A | 9/2000 | Radmand |
| 6,117,113 A | 9/2000 | Novacek |
| 6,127,320 A | 10/2000 | Ooij |
| 6,152,900 A | 11/2000 | Mayer |
| 6,156,010 A | 12/2000 | Kuracina |
| 6,159,185 A | 12/2000 | Tanihata |
| 6,162,196 A | 12/2000 | Hart |
| 6,171,287 B1 | 1/2001 | Lynn |
| 6,183,440 B1 | 2/2001 | Bell |
| 6,183,448 B1 | 2/2001 | Mayer |
| 6,193,690 B1 | 2/2001 | Dysarz |
| 6,200,262 B1 | 3/2001 | Ouchi |
| 6,203,527 B1 | 3/2001 | Zadini |
| 6,203,533 B1 | 3/2001 | Ouchi |
| 6,206,857 B1 | 3/2001 | Chen |
| 6,210,373 B1 | 4/2001 | Allmon |
| 6,213,978 B1 | 4/2001 | Voyten |
| 6,217,555 B1 | 4/2001 | Hart |
| 6,217,568 B1 | 4/2001 | Jepson |
| 6,221,047 B1 | 4/2001 | Greene |
| 6,221,050 B1 | 4/2001 | Ishida |
| 6,221,056 B1 | 4/2001 | Silverman |
| 6,224,569 B1 | 5/2001 | Brimhall |
| 6,228,060 B1 | 5/2001 | Howell |
| 6,234,999 B1 | 5/2001 | Wemmert |
| 6,235,003 B1 | 5/2001 | Dysarz |

(56) References Cited

U.S. PATENT DOCUMENTS

| | | |
|---|---|---|
| 6,235,006 B1 | 5/2001 | Dillon |
| 6,241,707 B1 | 6/2001 | Dysarz |
| 6,245,045 B1 | 6/2001 | Stratienko |
| 6,245,048 B1 | 6/2001 | Fangrow |
| 6,254,529 B1 | 7/2001 | Ouchi |
| 6,258,065 B1 | 7/2001 | Dennis |
| 6,261,264 B1 | 7/2001 | Tamaro |
| 6,261,265 B1 | 7/2001 | Mosseri |
| 6,273,869 B1 | 8/2001 | Vaillancourt |
| 6,277,100 B1 | 8/2001 | Raulerson |
| 6,280,419 B1 | 8/2001 | Vojtasek |
| 6,287,278 B1 | 9/2001 | Woehr |
| 6,287,279 B1 | 9/2001 | Siekmann |
| 6,287,280 B1 | 9/2001 | Lampropoulos |
| 6,306,124 B1 | 10/2001 | Jones |
| 6,322,537 B1 | 11/2001 | Chang |
| 6,322,541 B2 | 11/2001 | West |
| 6,342,045 B1 | 1/2002 | Somers |
| 6,344,031 B1 | 2/2002 | Novacek |
| 6,344,033 B1 | 2/2002 | Jepson |
| 6,352,520 B1 | 3/2002 | Miyazaki |
| 6,352,521 B1 | 3/2002 | Prosl |
| 6,358,265 B1 | 3/2002 | Thorne, Jr. |
| 6,379,332 B1 | 4/2002 | Van Landuyt |
| 6,379,333 B1 | 4/2002 | Brimhall |
| 6,379,372 B1 | 4/2002 | Dehdashtian |
| 6,394,983 B1 | 5/2002 | Mayoral |
| 6,402,721 B1 | 6/2002 | Lo |
| 6,406,459 B1 | 6/2002 | Allmon |
| 6,409,703 B1 | 6/2002 | Lu |
| 6,413,236 B1 | 7/2002 | Van Dyke |
| 6,416,499 B2 | 7/2002 | Paul, Jr. |
| 6,425,884 B1 | 7/2002 | Wemmert |
| 6,440,101 B1 | 8/2002 | Grabenkort |
| 6,443,927 B1 | 9/2002 | Cook |
| 6,443,929 B1 | 9/2002 | Kuracina |
| 6,461,328 B2 | 10/2002 | Wang |
| 6,475,194 B2 | 11/2002 | Domici, Jr. |
| 6,485,459 B1 | 11/2002 | Surowitz |
| 6,485,468 B2 | 11/2002 | Vojtasek |
| 6,488,656 B1 | 12/2002 | Wu |
| 6,488,663 B1 | 12/2002 | Steg |
| 6,488,674 B2 | 12/2002 | Becker |
| 6,506,181 B2 | 1/2003 | Meng |
| 6,520,939 B2 | 2/2003 | Lafontaine |
| 6,524,276 B1 | 2/2003 | Halseth |
| 6,524,278 B1 | 2/2003 | Campbell |
| 6,527,747 B2 | 3/2003 | Adams |
| 6,530,903 B2 | 3/2003 | Wang |
| 6,533,759 B1 | 3/2003 | Watson |
| 6,537,259 B1 | 3/2003 | Niermann |
| 6,545,242 B1 | 4/2003 | Butler |
| 6,551,283 B1 | 4/2003 | Guo |
| 6,569,119 B2 | 5/2003 | Haberland |
| 6,572,591 B2 | 6/2003 | Mayer |
| 6,582,402 B1 | 6/2003 | Erskine |
| 6,585,701 B1 | 7/2003 | Dysarz |
| 6,585,704 B2 | 7/2003 | Luther |
| 6,592,555 B1 | 7/2003 | Wen-Pi |
| 6,592,556 B1 | 7/2003 | Thorne |
| 6,595,954 B1 * | 7/2003 | Luther et al. .................. 604/110 |
| 6,595,955 B2 | 7/2003 | Ferguson |
| 6,595,964 B2 | 7/2003 | Finley |
| 6,595,965 B1 | 7/2003 | Utterberg |
| 6,595,981 B2 | 7/2003 | Huet |
| 6,602,240 B2 | 8/2003 | Hermann |
| 6,605,073 B1 | 8/2003 | Pressly, Sr. |
| 6,610,031 B1 | 8/2003 | Chin |
| 6,616,630 B1 | 9/2003 | Woehr |
| 6,616,640 B2 | 9/2003 | Chen |
| 6,620,136 B1 | 9/2003 | Pressly, Sr. |
| 6,623,458 B2 | 9/2003 | Woehr |
| 6,629,959 B2 | 10/2003 | Kuracina |
| 6,632,200 B2 | 10/2003 | Potter |
| 6,632,201 B1 | 10/2003 | Mathias |
| 6,641,564 B1 | 11/2003 | Kraus |
| 6,651,956 B2 | 11/2003 | Miller |
| 6,652,486 B2 | 11/2003 | Bialecki |
| 6,652,490 B2 | 11/2003 | Howell |
| 6,663,592 B2 | 12/2003 | Rhad |
| 6,663,599 B2 | 12/2003 | Osbourne |
| 6,669,666 B2 | 12/2003 | Lu |
| 6,669,681 B2 | 12/2003 | Dudar |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,706,022 B1 | 3/2004 | Leinsing |
| 6,709,419 B2 | 3/2004 | Woehr |
| 6,712,791 B2 | 3/2004 | Lui |
| 6,719,726 B2 | 4/2004 | Meng |
| 6,723,073 B2 | 4/2004 | Ley |
| 6,736,798 B2 | 5/2004 | Ohkubo |
| 6,743,199 B2 | 6/2004 | Shue |
| 6,749,588 B1 | 6/2004 | Howell |
| 6,761,704 B2 | 7/2004 | Crawford |
| 6,761,705 B1 | 7/2004 | Chiu |
| 6,761,706 B2 | 7/2004 | Vaillancourt |
| 6,764,468 B1 | 7/2004 | East |
| 6,767,340 B2 | 7/2004 | Willis |
| 6,770,059 B1 | 8/2004 | Spinks |
| 6,773,416 B1 | 8/2004 | Hsu |
| 6,776,774 B2 | 8/2004 | Tansey, Jr. |
| 6,796,962 B2 | 9/2004 | Ferguson |
| 6,796,968 B2 | 9/2004 | Ferguson |
| 6,796,969 B1 | 9/2004 | Andersson |
| 6,802,827 B2 | 10/2004 | Andersson |
| 6,808,161 B1 | 10/2004 | Hishikawa |
| 6,808,509 B1 | 10/2004 | Davey |
| 6,811,545 B2 | 11/2004 | Vaillancourt |
| 6,817,989 B2 | 11/2004 | Svendsen |
| 6,821,266 B2 | 11/2004 | Knepshield |
| 6,824,527 B2 | 11/2004 | Gollobin |
| 6,832,992 B2 | 12/2004 | Wilkinson |
| 6,855,127 B2 | 2/2005 | Nakagami |
| 6,855,130 B2 | 2/2005 | Saulenas |
| 6,860,869 B2 | 3/2005 | Dennis |
| 6,860,871 B2 | 3/2005 | Kuracina |
| 6,863,659 B2 | 3/2005 | Sharpe |
| 6,866,656 B2 | 3/2005 | Tingey |
| 6,878,131 B2 | 4/2005 | Novacek |
| 6,878,134 B2 | 4/2005 | Rogers |
| 6,883,778 B1 | 4/2005 | Newton |
| 6,884,224 B2 | 4/2005 | Dalton |
| 6,886,808 B2 | 5/2005 | Sarno |
| 6,893,423 B2 | 5/2005 | Denolly |
| 6,902,546 B2 | 6/2005 | Ferguson |
| 6,905,483 B2 | 6/2005 | Newby |
| 6,908,459 B2 | 6/2005 | Harding |
| 6,911,018 B2 | 6/2005 | Gordon |
| 6,913,595 B2 | 7/2005 | Mastorakis |
| 6,916,309 B2 | 7/2005 | Fangrow, Jr. |
| 6,916,311 B2 | 7/2005 | Vojtasek |
| 6,918,891 B2 | 7/2005 | Bressler |
| 6,921,382 B2 | 7/2005 | Lee |
| 6,921,386 B2 | 7/2005 | Shue |
| 6,926,698 B2 | 8/2005 | Lin |
| 6,926,700 B2 | 8/2005 | Bressler |
| 6,929,622 B2 | 8/2005 | Chian |
| 6,932,803 B2 | 8/2005 | Newby |
| 6,936,031 B2 | 8/2005 | Caleffi |
| 6,936,036 B2 | 8/2005 | Wilkinson |
| 6,942,642 B2 | 9/2005 | Suzuki |
| 6,958,055 B2 | 10/2005 | Donnan |
| 6,972,002 B2 | 12/2005 | Thorne |
| 6,979,314 B2 | 12/2005 | Hsieh |
| 6,981,965 B2 | 1/2006 | Luther |
| 6,984,213 B2 | 1/2006 | Horner |
| 6,986,759 B1 | 1/2006 | Jeremijevic |
| 6,991,215 B2 | 1/2006 | Kiehne |
| RE38,996 E | 2/2006 | Crawford |
| 6,997,902 B2 | 2/2006 | Thorne |

(56) References Cited

U.S. PATENT DOCUMENTS

| | | |
|---|---|---|
| 7,004,927 B2 | 2/2006 | Ferguson |
| 7,004,934 B2 | 2/2006 | Vaillancourt |
| 7,008,402 B2 | 3/2006 | Ferguson |
| 7,008,404 B2 | 3/2006 | Nakajima |
| 7,014,623 B2 | 3/2006 | Prestidge |
| 7,018,344 B2 | 3/2006 | Bressler |
| 7,018,365 B2 | 3/2006 | Strauss |
| 7,025,721 B2 | 4/2006 | Cohen |
| 7,025,744 B2 | 4/2006 | Utterberg |
| 7,033,339 B1 | 4/2006 | Lynn |
| 7,033,345 B2 | 4/2006 | Lee |
| 7,037,292 B2 | 5/2006 | Carlyon |
| 7,037,303 B2 | 5/2006 | Beaufore |
| 7,060,053 B2 | 6/2006 | Nakashima |
| 7,063,685 B2 | 6/2006 | Rome |
| 7,066,908 B2 | 6/2006 | Kuracina |
| 7,077,824 B2 | 7/2006 | Meyer |
| 7,081,106 B1 | 7/2006 | Guo |
| 7,083,596 B2 | 8/2006 | Saied |
| 7,083,600 B2 | 8/2006 | Meloul |
| 7,101,351 B2 | 9/2006 | Crawford |
| 7,101,353 B2 | 9/2006 | Lui |
| 7,104,970 B2 | 9/2006 | Chen |
| 7,112,191 B2 | 9/2006 | Daga |
| 7,125,396 B2 | 10/2006 | Leinsing |
| 7,125,397 B2 | 10/2006 | Woehr |
| 7,147,621 B2 | 12/2006 | Kiehne |
| 7,150,725 B2 | 12/2006 | Wilkinson |
| 7,160,269 B2 | 1/2007 | Woehr |
| 7,172,580 B2 | 2/2007 | Hruska |
| 7,175,610 B2 | 2/2007 | Mori |
| 7,179,244 B2 | 2/2007 | Smith |
| 7,182,734 B2 | 2/2007 | Saulenas |
| 7,186,239 B2 | 3/2007 | Woehr |
| 7,192,433 B2 | 3/2007 | Osypka |
| 7,198,618 B2 | 4/2007 | Ferguson |
| 7,207,975 B2 | 4/2007 | Miller |
| 7,214,208 B2 | 5/2007 | Vaillancourt |
| 7,214,211 B2 | 5/2007 | Woehr |
| 7,226,434 B2 | 6/2007 | Carlyon |
| 7,407,495 B2 | 8/2008 | Barere |
| 7,413,562 B2 | 8/2008 | Ferguson |
| 7,422,571 B2 | 9/2008 | Schweikert |
| 7,422,573 B2 | 9/2008 | Wilkinson |
| 7,445,611 B2 | 11/2008 | Osborne |
| 7,458,954 B2 | 12/2008 | Ferguson |
| 7,470,254 B2 | 12/2008 | Basta |
| 7,470,261 B2 | 12/2008 | Lynn |
| 7,470,262 B2 | 12/2008 | Hiejima |
| 7,497,847 B2 | 3/2009 | Crawford |
| 7,497,849 B2 | 3/2009 | Fangrow, Jr. |
| 7,500,965 B2 | 3/2009 | Menzi |
| 7,507,222 B2 | 3/2009 | Cindrich |
| 7,513,887 B2 | 4/2009 | Halseth |
| 7,513,888 B2 | 4/2009 | Sircom |
| 7,524,300 B2 | 4/2009 | Patton |
| 7,530,965 B2 | 5/2009 | Villa |
| 7,534,227 B2 | 5/2009 | Kulli |
| 7,534,231 B2 | 5/2009 | Kuracina |
| 7,537,582 B2 | 5/2009 | Suresh |
| 7,544,181 B2 | 6/2009 | Axelsson |
| 7,566,323 B2 | 7/2009 | Chang |
| 7,566,327 B2 | 7/2009 | Mathias |
| 7,569,033 B2 | 8/2009 | Greene |
| 7,572,247 B2 | 8/2009 | Smith |
| 7,575,570 B2 | 8/2009 | Barere |
| 7,578,803 B2 | 8/2009 | Rome |
| 7,578,805 B2 | 8/2009 | Hwang |
| 7,578,806 B2 | 8/2009 | Zeoli |
| 7,591,449 B2 | 9/2009 | Raines |
| 7,597,681 B2 | 10/2009 | Sutton |
| 7,597,684 B2 | 10/2009 | Alcha |
| 7,601,139 B2 | 10/2009 | Woehr |
| 7,604,616 B2 | 10/2009 | Thoresen |
| 7,608,057 B2 | 10/2009 | Woehr |
| 7,611,485 B2 | 11/2009 | Ferguson |
| 7,611,487 B2 | 11/2009 | Woehr |
| 7,611,488 B2 | 11/2009 | Chang |
| 7,611,499 B2 | 11/2009 | Woehr |
| 7,614,423 B2 | 11/2009 | Yokota |
| 7,618,395 B2 | 11/2009 | Ferguson |
| 7,625,360 B2 | 12/2009 | Woehr |
| 7,628,774 B2 | 12/2009 | Fangrow, Jr. |
| 7,628,776 B2 | 12/2009 | Gibson |
| 7,632,243 B2 | 12/2009 | Bialecki |
| 7,635,352 B2 | 12/2009 | Adams |
| 7,635,357 B2 | 12/2009 | Mayer |
| 7,637,887 B2 | 12/2009 | Woehr |
| 7,637,888 B2 | 12/2009 | Schwarzbich |
| 7,637,893 B2 | 12/2009 | Christensen |
| 7,651,476 B2 | 1/2010 | Kohler |
| 7,651,481 B2 | 1/2010 | Raybuck |
| 7,654,988 B2 | 2/2010 | Moulton |
| 7,658,725 B2 | 2/2010 | Bialecki |
| 7,662,134 B2 | 2/2010 | Miller |
| 7,666,170 B2 | 2/2010 | Guala |
| 7,670,317 B2 | 3/2010 | Cindrich |
| 7,670,320 B2 | 3/2010 | Iwase |
| 7,682,331 B2 | 3/2010 | Carrez |
| 7,682,339 B2 | 3/2010 | Fujii |
| 7,682,340 B2 | 3/2010 | Funamura |
| 7,686,784 B2 | 3/2010 | Baik |
| 7,691,088 B2 | 4/2010 | Howell |
| 7,694,403 B2 | 4/2010 | Moulton |
| 7,713,242 B2 | 5/2010 | Streifinger |
| 7,713,243 B2 | 5/2010 | Hillman |
| 7,713,250 B2 | 5/2010 | Harding |
| 7,713,256 B2 | 5/2010 | Brimhall |
| 7,713,257 B2 | 5/2010 | Brimhall |
| 7,717,888 B2 | 5/2010 | Vaillancourt |
| 7,722,563 B2 | 5/2010 | Isaacson |
| 7,722,564 B2 | 5/2010 | Vaillancourt |
| 7,722,569 B2 | 5/2010 | Soderholm |
| 7,727,198 B2 | 6/2010 | Nakajima |
| 7,731,687 B2 | 6/2010 | Menzi |
| 7,731,694 B2 | 6/2010 | Becker |
| 7,736,332 B2 | 6/2010 | Carlyon |
| 7,736,337 B2 | 6/2010 | Diep |
| 7,736,339 B2 | 6/2010 | Woehr |
| 7,736,340 B2 | 6/2010 | Harding |
| 7,736,342 B2 | 6/2010 | Abriles |
| 7,740,613 B2 | 6/2010 | Yokoi |
| 7,740,614 B2 | 6/2010 | Murashita |
| 7,744,567 B2 | 6/2010 | Glowacki |
| 7,744,568 B2 | 6/2010 | Douglas |
| 7,744,570 B2 | 6/2010 | Fangrow, Jr. |
| 7,753,338 B2 | 7/2010 | Desecki |
| 7,753,877 B2 | 7/2010 | Bialecki |
| 7,753,887 B2 | 7/2010 | Botich |
| 7,758,543 B2 | 7/2010 | Ferraresi |
| 7,762,986 B2 | 7/2010 | Wang |
| 7,763,199 B2 | 7/2010 | Fangrow, Jr. |
| 7,771,412 B2 | 8/2010 | Anderson |
| 7,785,296 B2 | 8/2010 | Muskatello |
| 7,794,445 B2 | 9/2010 | Dalton |
| 7,794,675 B2 | 9/2010 | Lynn |
| 7,798,994 B2 | 9/2010 | Brimhall |
| 7,806,849 B2 | 10/2010 | Woehr |
| 7,806,858 B2 | 10/2010 | Smith |
| 7,806,869 B2 | 10/2010 | Nilsson |
| 7,806,890 B2 | 10/2010 | McKinnon |
| 7,811,261 B2 | 10/2010 | Rubinstein |
| 7,815,614 B2 | 10/2010 | Fangrow, Jr. |
| 7,824,393 B2 | 11/2010 | Fangrow |
| 7,828,773 B2 | 11/2010 | Swisher |
| 7,828,774 B2 | 11/2010 | Harding |
| 7,833,199 B2 | 11/2010 | Franer |
| 7,850,648 B2 | 12/2010 | Gratwohl |
| 7,850,650 B2 | 12/2010 | Breitweiser |
| 7,850,652 B2 | 12/2010 | Liniger |
| 7,867,204 B2 | 1/2011 | Bartholomew |
| 7,887,516 B2 | 2/2011 | Young |
| 7,892,209 B2 | 2/2011 | Harand |
| 7,892,216 B2 | 2/2011 | Fangrow, Jr. |

(56) References Cited

U.S. PATENT DOCUMENTS

| | | |
|---|---|---|
| 7,901,379 B2 | 3/2011 | Argentine |
| 7,905,857 B2 | 3/2011 | Swisher |
| 7,914,488 B2 | 3/2011 | Dickerson |
| 7,914,494 B2 | 3/2011 | Hiejima |
| 7,914,519 B2 | 3/2011 | Moran |
| 7,922,698 B2 | 4/2011 | Riesenberger |
| 7,927,314 B2 | 4/2011 | Kuracina |
| 7,931,615 B2 | 4/2011 | Fangrow, Jr. |
| 7,931,622 B2 | 4/2011 | Beling |
| 7,935,080 B2 | 5/2011 | Howell |
| 7,935,090 B2 | 5/2011 | Patton |
| 7,938,805 B2 | 5/2011 | Harding |
| 7,947,018 B2 | 5/2011 | Mckinnon |
| 7,947,032 B2 | 5/2011 | Harding |
| 7,951,119 B2 | 5/2011 | Leeflang |
| 7,951,122 B2 | 5/2011 | Shekalim |
| 7,955,306 B2 | 6/2011 | Wyss |
| 7,959,613 B2 | 6/2011 | Rhad |
| 7,967,797 B2 | 6/2011 | Winsor |
| 7,972,300 B2 | 7/2011 | Smith |
| 7,972,313 B2 | 7/2011 | Woehr |
| 7,976,498 B2 | 7/2011 | Swisher |
| 7,976,502 B2 | 7/2011 | Baid |
| 7,976,503 B2 | 7/2011 | Khan |
| 7,981,090 B2 | 7/2011 | Plishka |
| 7,985,199 B2 | 7/2011 | Kornerup |
| 7,985,232 B2 | 7/2011 | Potter |
| 7,988,664 B2 | 8/2011 | Fiser |
| 7,993,305 B2 | 8/2011 | Ye |
| 7,993,306 B2 | 8/2011 | Marrs |
| 7,998,122 B2 | 8/2011 | Lynn |
| 8,002,765 B2 | 8/2011 | Lopez |
| 8,006,953 B2 | 8/2011 | Bennett |
| 8,016,791 B2 | 9/2011 | Sugiki |
| 8,021,343 B2 | 9/2011 | Nalesso |
| 8,025,646 B2 | 9/2011 | Fukai |
| 8,029,472 B2 | 10/2011 | Leinsing |
| 8,038,647 B2 | 10/2011 | Harding |
| 8,043,263 B2 | 10/2011 | Helgeson |
| 8,043,266 B2 | 10/2011 | Murashita |
| 8,043,316 B2 | 10/2011 | Hardin |
| 8,048,031 B2 | 11/2011 | Shaw |
| 8,048,039 B2 | 11/2011 | Carlyon |
| 8,052,646 B2 | 11/2011 | Schweikert |
| 8,052,647 B2 | 11/2011 | Raulerson |
| 8,052,653 B2 | 11/2011 | Gratwohl |
| 8,062,261 B2 | 11/2011 | Adams |
| 8,066,670 B2 | 11/2011 | Cluff |
| 8,075,529 B2 | 12/2011 | Nakajima |
| RE43,141 E | 1/2012 | Halseth |
| 8,088,104 B2 | 1/2012 | Smith |
| 8,096,973 B2 | 1/2012 | Snow |
| 8,100,857 B2 | 1/2012 | Kuracina |
| 8,100,858 B2 | 1/2012 | Woehr |
| 8,105,276 B2 | 1/2012 | Chen |
| 8,123,738 B2 | 2/2012 | Vaillancourt |
| 8,128,594 B1 | 3/2012 | Chang |
| 8,133,207 B2 | 3/2012 | Wilkinson |
| 8,133,209 B2 | 3/2012 | Guala |
| 8,137,321 B2 | 3/2012 | Argentine |
| 8,147,455 B2 | 4/2012 | Butts |
| 8,157,768 B2 | 4/2012 | Haider |
| 8,162,881 B2 | 4/2012 | Lilley, Jr. |
| 8,162,889 B2 | 4/2012 | Swisher |
| 8,162,904 B2 | 4/2012 | Takano |
| 8,197,452 B2 | 6/2012 | Harding |
| 8,206,355 B2 | 6/2012 | Thorne |
| 8,211,070 B2 | 7/2012 | Woehr |
| 8,226,627 B2 | 7/2012 | Fowles |
| 8,231,525 B2 | 7/2012 | Cohen |
| 8,251,950 B2 | 8/2012 | Albert |
| 8,257,313 B2 * | 9/2012 | McKinnon et al. ...... 604/164.08 |
| 8,257,322 B2 | 9/2012 | Koehler |
| 2001/0021821 A1 | 9/2001 | Wang |
| 2001/0021827 A1 | 9/2001 | Ferguson |
| 2001/0039401 A1 | 11/2001 | Ferguson |
| 2002/0010434 A1 | 1/2002 | Larsen |
| 2002/0022803 A1 | 2/2002 | Wemmert |
| 2002/0026154 A1 | 2/2002 | Chang |
| 2002/0065488 A1 | 5/2002 | Suzuki |
| 2002/0065489 A1 | 5/2002 | Novacek |
| 2002/0128604 A1 | 9/2002 | Nakajima |
| 2002/0151850 A1 | 10/2002 | Ferguson |
| 2002/0156428 A1 | 10/2002 | Lee |
| 2003/0060785 A1 | 3/2003 | Lavean |
| 2003/0105431 A1 | 6/2003 | Howell |
| 2003/0114797 A1 | 6/2003 | Vaillancourt |
| 2003/0125676 A1 | 7/2003 | Swenson |
| 2003/0125677 A1 | 7/2003 | Swenson |
| 2003/0130623 A1 | 7/2003 | Chen |
| 2003/0144627 A1 | 7/2003 | Woehr |
| 2003/0181867 A1 | 9/2003 | Bressler |
| 2003/0181869 A1 | 9/2003 | Swenson |
| 2003/0181870 A1 | 9/2003 | Bressler |
| 2003/0181871 A1 | 9/2003 | Wilkinson |
| 2003/0181875 A1 | 9/2003 | Bressler |
| 2003/0195471 A1 | 10/2003 | Woehr |
| 2003/0195479 A1 | 10/2003 | Kuracina |
| 2003/0199827 A1 | 10/2003 | Thorne |
| 2003/0216687 A1 | 11/2003 | Hwang |
| 2003/0229316 A1 | 12/2003 | Hwang |
| 2004/0006313 A1 | 1/2004 | Chian |
| 2004/0019334 A1 | 1/2004 | Ohkubo |
| 2004/0039333 A1 | 2/2004 | Lee |
| 2004/0044313 A1 | 3/2004 | Nakajima |
| 2004/0049155 A1 | 3/2004 | Schramm |
| 2004/0078003 A1 | 4/2004 | Smith |
| 2004/0092871 A1 | 5/2004 | Knepshield |
| 2004/0106903 A1 | 6/2004 | Shue |
| 2004/0116857 A1 | 6/2004 | Kiehne |
| 2004/0122378 A1 | 6/2004 | Hsu |
| 2004/0138628 A1 | 7/2004 | Woehr |
| 2004/0147876 A1 | 7/2004 | Maggioni |
| 2004/0171989 A1 | 9/2004 | Horner |
| 2004/0171995 A1 | 9/2004 | Niermann |
| 2004/0186426 A1 | 9/2004 | Allard |
| 2004/0186427 A1 | 9/2004 | Pok |
| 2004/0186434 A1 | 9/2004 | Harding |
| 2004/0204681 A1 | 10/2004 | Thoresen |
| 2004/0225260 A1 | 11/2004 | Villa |
| 2004/0230164 A1 | 11/2004 | Spinks |
| 2004/0236288 A1 | 11/2004 | Howell |
| 2004/0236289 A1 | 11/2004 | Ferguson |
| 2004/0243060 A1 | 12/2004 | Rossi |
| 2004/0243061 A1 | 12/2004 | McGurk |
| 2004/0243066 A1 | 12/2004 | Meyer |
| 2004/0243071 A1 | 12/2004 | Suzuki |
| 2005/0004532 A1 | 1/2005 | Woehr |
| 2005/0027263 A1 | 2/2005 | Woehr |
| 2005/0038385 A1 | 2/2005 | Shen |
| 2005/0038399 A1 | 2/2005 | Suzuki |
| 2005/0043691 A1 | 2/2005 | Ferguson |
| 2005/0049554 A1 | 3/2005 | Chueh |
| 2005/0059933 A1 | 3/2005 | Johnson |
| 2005/0070855 A1 | 3/2005 | Ferguson |
| 2005/0075609 A1 | 4/2005 | Latona |
| 2005/0080378 A1 | 4/2005 | Cindrich |
| 2005/0085745 A1 | 4/2005 | Kitta |
| 2005/0096599 A1 | 5/2005 | Crawford |
| 2005/0119627 A1 | 6/2005 | Crawford |
| 2005/0137528 A1 | 6/2005 | Wilkinson |
| 2005/0137535 A1 | 6/2005 | Gollobin |
| 2005/0159706 A1 | 7/2005 | Wilkinson |
| 2005/0182362 A1 | 8/2005 | Sircom |
| 2005/0215951 A1 | 9/2005 | Saulenas |
| 2005/0234408 A1 | 10/2005 | Chong |
| 2005/0240150 A1 | 10/2005 | Gordon |
| 2005/0267412 A1 | 12/2005 | Wilkinson |
| 2006/0058742 A1 | 3/2006 | Cha |
| 2006/0074384 A1 | 4/2006 | Kohler |
| 2006/0079808 A1 | 4/2006 | Allard |
| 2006/0084916 A1 | 4/2006 | Lo |
| 2006/0106339 A1 | 5/2006 | Mastorakis |
| 2006/0106340 A1 | 5/2006 | Goossens |

(56) References Cited

U.S. PATENT DOCUMENTS

| | | |
|---|---|---|
| 2006/0116638 A1 | 6/2006 | Woehr |
| 2006/0155245 A1 | 7/2006 | Woehr |
| 2006/0161108 A1 | 7/2006 | Mogensen |
| 2006/0161116 A1 | 7/2006 | Willis |
| 2006/0184115 A1 | 8/2006 | Saied |
| 2006/0189934 A1 | 8/2006 | Kuracina |
| 2006/0200195 A1 | 9/2006 | Yang |
| 2006/0217655 A1 | 9/2006 | Vitullo |
| 2006/0229554 A1 | 10/2006 | Lou |
| 2006/0229556 A1 | 10/2006 | Pressly, Jr. |
| 2006/0229563 A1 | 10/2006 | O'Reagan |
| 2006/0253074 A1 | 11/2006 | Thayer |
| 2006/0253076 A1 | 11/2006 | Butts |
| 2006/0264827 A1 | 11/2006 | Whang |
| 2006/0264828 A1 | 11/2006 | Woehr |
| 2007/0005013 A1 | 1/2007 | Lai |
| 2007/0005014 A1 | 1/2007 | Lin |
| 2007/0016139 A1 | 1/2007 | Breitweiser |
| 2007/0038179 A1 | 2/2007 | Bialecki |
| 2007/0038182 A1 | 2/2007 | Bialecki |
| 2007/0038183 A1 | 2/2007 | Bialecki |
| 2007/0038184 A1 | 2/2007 | Bialecki |
| 2007/0038185 A1 | 2/2007 | Albert |
| 2007/0038186 A1 | 2/2007 | Sutton |
| 2007/0038187 A1 | 2/2007 | Albert |
| 2007/0038188 A1 | 2/2007 | Bialecki |
| 2007/0073221 A1 | 3/2007 | Bialecki |
| 2007/0073222 A1 | 3/2007 | Lilley, Jr. |
| 2007/0073225 A1 | 3/2007 | Lee |
| 2007/0078390 A1 | 4/2007 | Cing-hong |
| 2007/0078397 A1 | 4/2007 | Weststrate |
| 2007/0078404 A1 | 4/2007 | Wu |
| 2007/0078405 A1 | 4/2007 | Lai |
| 2007/0078407 A1 | 4/2007 | Huang |
| 2007/0083162 A1 | 4/2007 | O'Reagan |
| 2007/0083167 A1 | 4/2007 | Smith |
| 2007/0100296 A1 | 5/2007 | Hwang |
| 2007/0100297 A1 | 5/2007 | Woehr |
| 2007/0106231 A1 | 5/2007 | Snow |
| 2007/0118082 A1 | 5/2007 | Mori |
| 2007/0135764 A1 | 6/2007 | Chen |
| 2007/0156093 A1 | 7/2007 | Woehr |
| 2007/0156100 A1 | 7/2007 | Moesli |
| 2007/0161950 A1 | 7/2007 | Carlyon |
| 2007/0179443 A1 | 8/2007 | Johnson aka Mindes |
| 2007/0179446 A1 | 8/2007 | Carrez |
| 2007/0197964 A1 | 8/2007 | Hsu |
| 2007/0197965 A1 | 8/2007 | Hsu |
| 2007/0197966 A1 | 8/2007 | Lee |
| 2007/0197967 A1 | 8/2007 | Lee |
| 2007/0219492 A1 | 9/2007 | Lucas |
| 2007/0232998 A1 | 10/2007 | Yang |
| 2007/0250003 A1 | 10/2007 | Bare |
| 2007/0255212 A1 | 11/2007 | Smith |
| 2007/0270753 A1 | 11/2007 | Kulli |
| 2007/0282268 A1 | 12/2007 | Mayse |
| 2008/0021388 A1 | 1/2008 | Schwarzich |
| 2008/0027381 A1 | 1/2008 | Smith |
| 2008/0065015 A1 | 3/2008 | Fiser |
| 2008/0065025 A1 | 3/2008 | Jenkins |
| 2008/0071213 A1 | 3/2008 | Sircom |
| 2008/0071222 A1 | 3/2008 | Rhad |
| 2008/0086089 A1 | 4/2008 | Isaacson |
| 2008/0097304 A1 | 4/2008 | Thorne |
| 2008/0097342 A1 | 4/2008 | Gordin |
| 2008/0097343 A1 | 4/2008 | Woehr |
| 2008/0097344 A1* | 4/2008 | McKinnon et al. ........... 604/263 |
| 2008/0097345 A1 | 4/2008 | Ferguson |
| 2008/0103449 A1 | 5/2008 | Murashita |
| 2008/0108944 A1 | 5/2008 | Woehr |
| 2008/0115845 A1 | 5/2008 | Leuliet |
| 2008/0119795 A1 | 5/2008 | Erskine |
| 2008/0140011 A1 | 6/2008 | Hager |
| 2008/0147003 A1 | 6/2008 | Menzi |
| 2008/0154195 A1 | 6/2008 | Huang |
| 2008/0177238 A1 | 7/2008 | Follman |
| 2008/0243086 A1* | 10/2008 | Hager et al. ................... 604/198 |
| 2008/0249478 A1 | 10/2008 | Ishikura |
| 2008/0249480 A1 | 10/2008 | Riesenberger |
| 2008/0283789 A1 | 11/2008 | Rubio |
| 2008/0312596 A1 | 12/2008 | Murashita |
| 2009/0005743 A1 | 1/2009 | Vaillancourt |
| 2009/0012480 A1 | 1/2009 | Moulton |
| 2009/0048566 A1 | 2/2009 | Ferguson |
| 2009/0054852 A1 | 2/2009 | Takano |
| 2009/0082732 A1 | 3/2009 | Hillman |
| 2009/0088696 A1 | 4/2009 | Harding |
| 2009/0093771 A1 | 4/2009 | Hwang |
| 2009/0131876 A1 | 5/2009 | Coyne |
| 2009/0137958 A1 | 5/2009 | Erskine |
| 2009/0143737 A1 | 6/2009 | Kobayashi |
| 2009/0157013 A1 | 6/2009 | Wong |
| 2009/0163861 A1 | 6/2009 | Carlyon |
| 2009/0171285 A1 | 7/2009 | Wang |
| 2009/0177167 A1 | 7/2009 | Kuracina |
| 2009/0182280 A1 | 7/2009 | Glowacki |
| 2009/0216153 A1 | 8/2009 | Srivatsa |
| 2009/0216201 A1 | 8/2009 | Meehan |
| 2009/0227956 A1 | 9/2009 | Emmott |
| 2009/0281499 A1 | 11/2009 | Harding |
| 2009/0281506 A1 | 11/2009 | Mathias |
| 2009/0287154 A1 | 11/2009 | Harding |
| 2009/0292260 A1 | 11/2009 | Vaillancourft |
| 2009/0292261 A1 | 11/2009 | Greene |
| 2009/0306591 A1 | 12/2009 | Amisar |
| 2009/0312711 A1 | 12/2009 | Brimhall |
| 2010/0063455 A1 | 3/2010 | Moyer |
| 2010/0069840 A1 | 3/2010 | Suresh |
| 2010/0082002 A1 | 4/2010 | Baid |
| 2010/0087787 A1 | 4/2010 | Woehr |
| 2010/0106092 A1 | 4/2010 | Tanabe |
| 2010/0114035 A1 | 5/2010 | Schubert |
| 2010/0114036 A1 | 5/2010 | Steyn |
| 2010/0137815 A1 | 6/2010 | Kuracina |
| 2010/0191188 A1 | 7/2010 | Harding |
| 2010/0191189 A1 | 7/2010 | Harding |
| 2010/0198152 A1 | 8/2010 | Haindl |
| 2010/0204652 A1 | 8/2010 | Morrissey |
| 2010/0204654 A1 | 8/2010 | Mulholland |
| 2010/0222739 A1 | 9/2010 | Klippenstein |
| 2010/0222745 A1 | 9/2010 | Burkholz |
| 2010/0222746 A1 | 9/2010 | Burkholz |
| 2010/0228197 A1 | 9/2010 | Murashita |
| 2010/0234804 A1 | 9/2010 | Hiejima |
| 2010/0241087 A1 | 9/2010 | Moulton |
| 2010/0249707 A1* | 9/2010 | Woehr et al. ............. 604/164.08 |
| 2010/0286611 A1 | 11/2010 | Schraga |
| 2010/0298770 A1 | 11/2010 | Rubinstein |
| 2010/0324484 A1 | 12/2010 | Smith |
| 2010/0331781 A1 | 12/2010 | Millerd |
| 2011/0015573 A1 | 1/2011 | Maan |
| 2011/0015579 A1 | 1/2011 | Swisher |
| 2011/0024664 A1 | 2/2011 | Burnard |
| 2011/0054398 A1 | 3/2011 | Djordjevic |
| 2011/0054402 A1 | 3/2011 | Tanabe |
| 2011/0054403 A1 | 3/2011 | Tanabe |
| 2011/0060286 A1 | 3/2011 | Tanabe |
| 2011/0060294 A1 | 3/2011 | Baid |
| 2011/0066107 A1 | 3/2011 | Stephens |
| 2011/0066197 A1 | 3/2011 | Jaax |
| 2011/0092914 A1 | 4/2011 | Clayson |
| 2011/0098641 A1 | 4/2011 | Haider |
| 2011/0118673 A1 | 5/2011 | Dringenberg |
| 2011/0125056 A1 | 5/2011 | Merchant |
| 2011/0152782 A1 | 6/2011 | Jones |
| 2011/0152832 A1 | 6/2011 | Foshee |
| 2011/0160662 A1 | 6/2011 | Stout |
| 2011/0160663 A1 | 6/2011 | Stout |
| 2011/0160675 A1 | 6/2011 | Ruan |
| 2011/0208124 A1 | 8/2011 | Rhad |
| 2011/0208126 A1 | 8/2011 | Riemelmoser |
| 2011/0208133 A1 | 8/2011 | Woehr |
| 2011/0213307 A1 | 9/2011 | Kawai |
| 2011/0264037 A1 | 10/2011 | Foshee |

(56) References Cited

U.S. PATENT DOCUMENTS

| | | |
|---|---|---|
| 2011/0264040 A1 | 10/2011 | Li |
| 2011/0275991 A1 | 11/2011 | Thayer |
| 2011/0282285 A1 | 11/2011 | Blanchard |
| 2011/0282286 A1 | 11/2011 | Argentine |
| 2011/0301542 A1 | 12/2011 | Schwartz |
| 2011/0301551 A1 | 12/2011 | Koehler |
| 2011/0319820 A1 | 12/2011 | Teoh |
| 2012/0016301 A1 | 1/2012 | Stout |
| 2012/0016302 A1 | 1/2012 | Stout |
| 2012/0022498 A1 | 1/2012 | Smith |
| 2012/0035552 A1 | 2/2012 | Woehr |
| 2012/0041374 A1 | 2/2012 | Lee |
| 2012/0046620 A1 | 2/2012 | Woehr |
| 2012/0046621 A1 | 2/2012 | Vaillancourt |
| 2012/0059323 A1 | 3/2012 | Moberg |
| 2012/0059325 A1 | 3/2012 | Cluff |
| 2012/0078200 A1 | 3/2012 | Woehr |
| 2012/0130321 A1 | 5/2012 | Woehr |
| 2012/0136311 A1 | 5/2012 | Knutsson |
| 2012/0143138 A1 | 6/2012 | King |
| 2012/0143151 A1 | 6/2012 | Low |
| 2012/0184910 A1 | 7/2012 | Woehr |
| 2012/0197201 A1 | 8/2012 | Tanabe |
| 2012/0215179 A1 | 8/2012 | Halili |
| 2012/0220956 A1 | 8/2012 | Kuracina |
| 2012/0220957 A1 * | 8/2012 | Kuracina et al. .............. 604/263 |

OTHER PUBLICATIONS

U.S. Appl. No. 13/651,979, filed Oct. 15, 2012, Walker et al.
European Search Report dated Jul. 26, 2012 in copending European Appln. No. 12165851.
International Search Report dated Dec. 17, 2012 in copending International Application No. PCT/2012/055295.
International Search Report dated Dec. 19, 2012 in copending International Application No. PCT/US2012/056979.
International Search Report dated Jan. 16, 2013 in copending International Application No. PCT/US2012/060240.

* cited by examiner

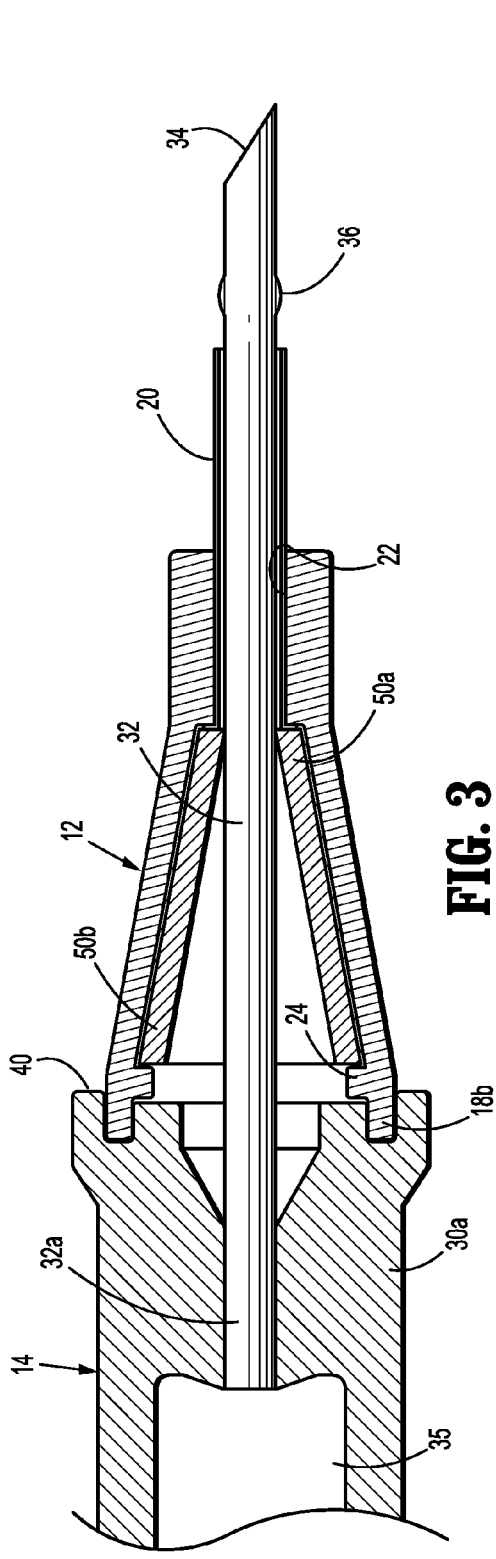
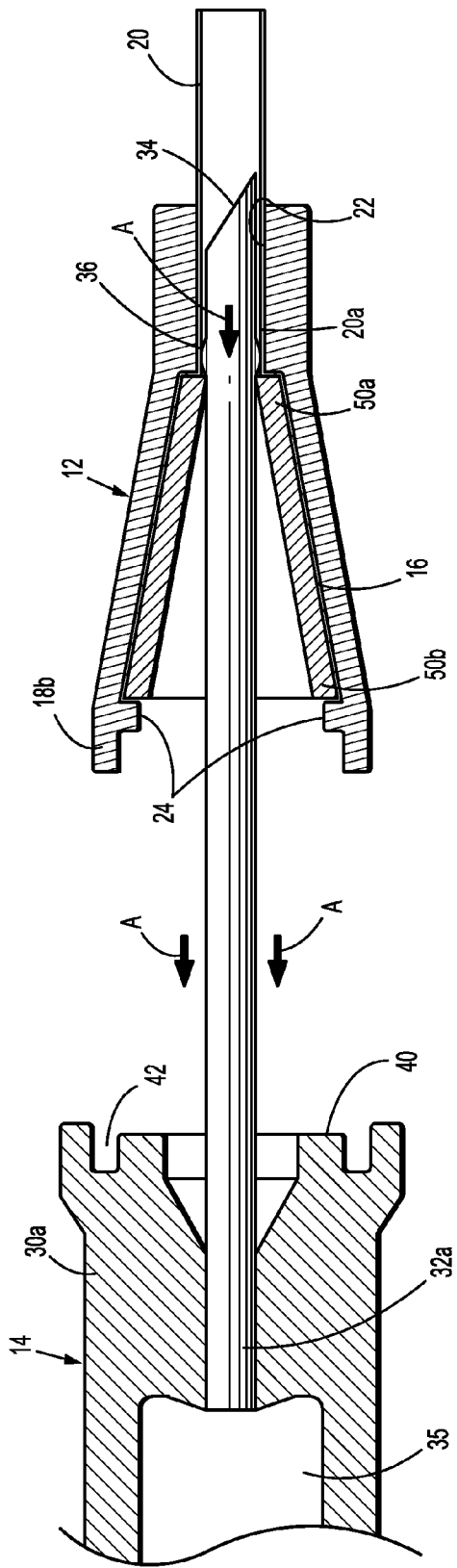
FIG. 3
FIG. 4

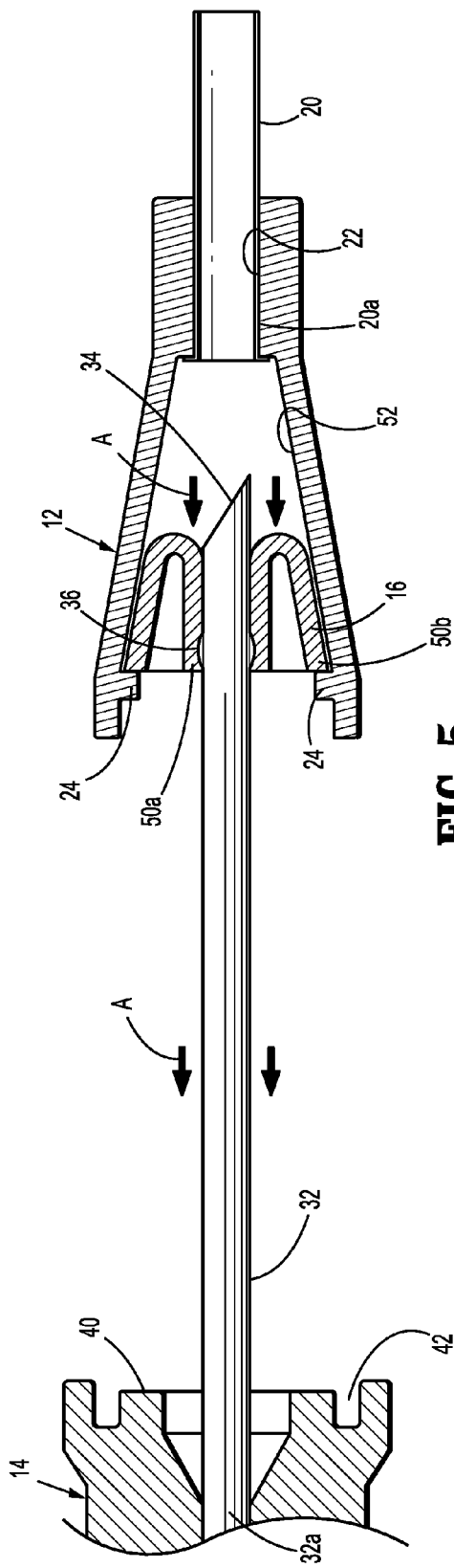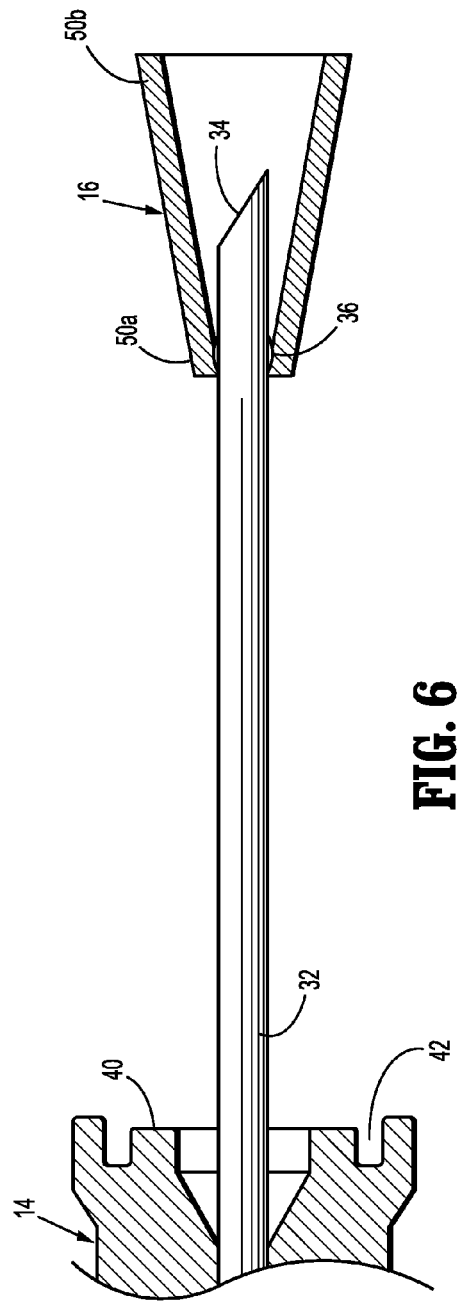

SAFETY CATHETER AND NEEDLE ASSEMBLY

CROSS REFERENCE TO RELATED APPLICATION

This application claims the benefit of and priority to U.S. Provisional Application Ser. No. 61/539,153 which was filed on Sep. 26, 2011, the entirety of which is incorporated herein by reference.

TECHNICAL FIELD

The present disclosure relates to a needle assembly including a needle guard for use in medical procedures, and in particular to intravenous ("I.V.") catheter assemblies including a needle assembly that includes a needle tip guard to cover a tip of a needle to prevent accidental needle sticks.

BACKGROUND

There are a variety of needles available for different medical and surgical uses. For example, intravenous catheters are utilized in various applications for supplying or withdrawing fluids to or from the body. The intravenous catheter includes an external cannula for indwelling in a blood vessel of a patient and an internal needle that is inserted into the external cannula to facilitate smooth piercing of the blood vessel of the patient. In operation, the internal needle is inserted into the external cannula such that the tip portion of the internal needle protrudes from a tip portion of the external cannula. The internal needle is manipulated to pierce a blood vessel and to position the external cannula within the blood vessel. Then, while the external cannula indwells in the blood vessel, the internal needle is withdrawn from the external cannula. With the external cannula positioned within a blood vessel, a medical device can be connected to the rear end portion of the external cannula using, for example, a luer connector, to facilitate the supply and withdrawal of fluid, e.g., blood, medication, etc., to or from the body.

After the internal needle is withdrawn from the external cannula, the exposed needle tip creates a danger of accidental needle stick which can leave a clinician vulnerable to the transmission of various blood-borne pathogens, such as HIV and hepatitis. While needle tip protectors have been developed to protect the clinician from needle stick injuries, the cost, ease of use, and effectiveness of these needle tip protectors leaves room for improvement.

Therefore, it would be beneficial to have a needle tip guard that is easily activated by a clinician, adequately protects the clinician from accidental needle stick injury, and is economical to produce.

SUMMARY

An IV catheter and safety needle assembly is provided which includes a catheter assembly, a needle assembly and a needle guard. The catheter assembly includes a catheter hub defining a receptacle and a tubular catheter extending distally from and in fluid communication with the receptacle. The catheter hub includes one or more protrusions extending from an inner wall of the catheter hub into the receptacle. The needle assembly includes a needle hub defining a chamber and a needle in fluid communication with the chamber. The needle has a sharpened distal tip and an enlarged diameter portion disposed proximally of the distal tip. The needle is dimensioned to extend through the catheter assembly such that the sharpened tip extends from a distal end of the tubular catheter. The needle guard is supported within the receptacle and has a proximal end positioned adjacent to the one or more protrusions and a distal end having an inner diameter which is smaller than the enlarged diameter portion of the needle. Upon withdrawal of the needle from the catheter assembly, the enlarged diameter of the needle is positioned to engage the distal end of the needle guard to move the needle guard into the one or more protrusions and effect an inversion of the needle guard about the sharpened tip of the needle.

In one embodiment, the enlarged diameter portion of the needle defines a crimp. Alternately, the enlarged diameter portion of the needle may include a protuberance formed on the needle.

The needle guard may define a conical throughbore having a diameter at a proximal end which is larger than the inner diameter at the distal end. In addition, the needle guard may also have a conical configuration.

In one embodiment, the needle hub defines a flashback chamber and is formed from a transparent material. The needle guard may include a cutout formed in an outer surface of the needle guard which is positioned and configured to receive the enlarged diameter portion of the needle upon inversion of the needle guard. The enlarged diameter portion of the needle is configured to resist removal of the enlarged diameter portion from the cutout. In the alternative, the enlarged diameter portion of the needle may be dimensioned to frictionally engage the inner diameter of the needle guard after inversion of the needle to retain the needle guard on the tip of the needle.

BRIEF DESCRIPTION OF THE DRAWINGS

Various embodiments of the present disclosure will be described herein with references to the accompanying drawings, wherein:

FIG. 3 is a side cross-sectional view of the IV catheter and safety needle assembly taken along section lines 3-3 of FIG. 1;

FIG. 4 is a side cross-sectional view of the IV catheter and safety needle assembly shown in FIG. 3 as the needle assembly is being separated from the catheter assembly;

FIG. 5 is a side cross-sectional view of the IV catheter and safety needle assembly shown in FIG. 4 as the needle assembly is being separated from the catheter assembly and the needle tip guard is being inverted;

FIG. 6 is a side cross-sectional view of the needle assembly and needle guard after the needle assembly has been separated from the catheter assembly and the needle tip guard has been inverted about the needle tip;

DETAILED DESCRIPTION OF THE EMBODIMENTS

Figure 1:
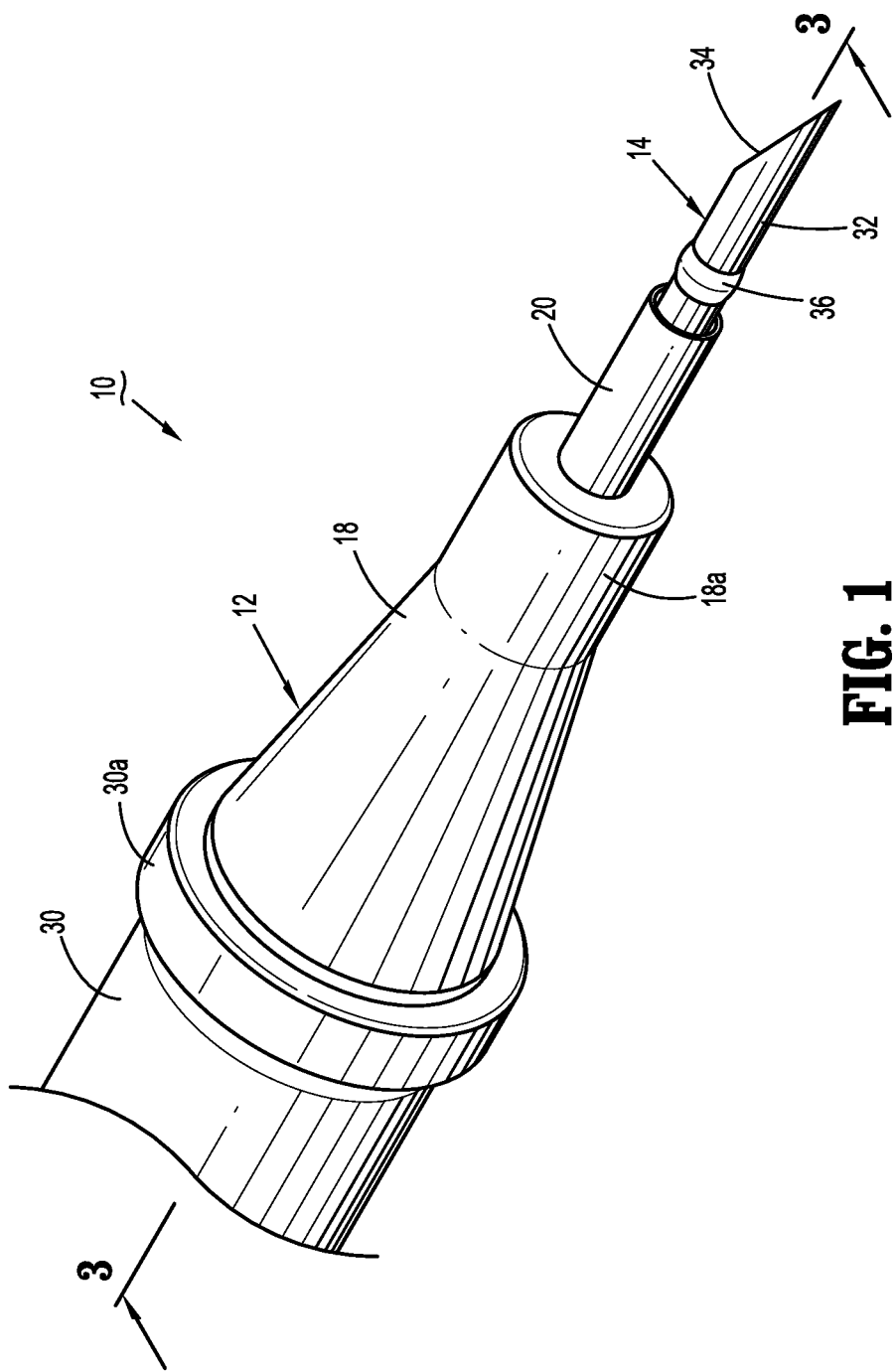
FIG. 1 is a perspective view of the distal end of one embodiment of the presently disclosed IV catheter and safety needle assembly.

Various exemplary embodiments of the presently disclosed IV catheter and safety needle assembly are described herein with reference to the drawings, wherein like reference numerals identify corresponding elements in each of the several views. In the following discussion, the term "proximal" should be understood as referring to the portion of a device or structure that is closer to a clinician during proper use and the term "distal" should be understood as referring to the portion of a device or structure that is further from the clinician during proper use. In addition, the term "patient" should be understood to refer to a human or other animal and the term "clinician" should be understood to refer to a doctor, nurse, or other care provider and may include support personnel.

Figure 2:
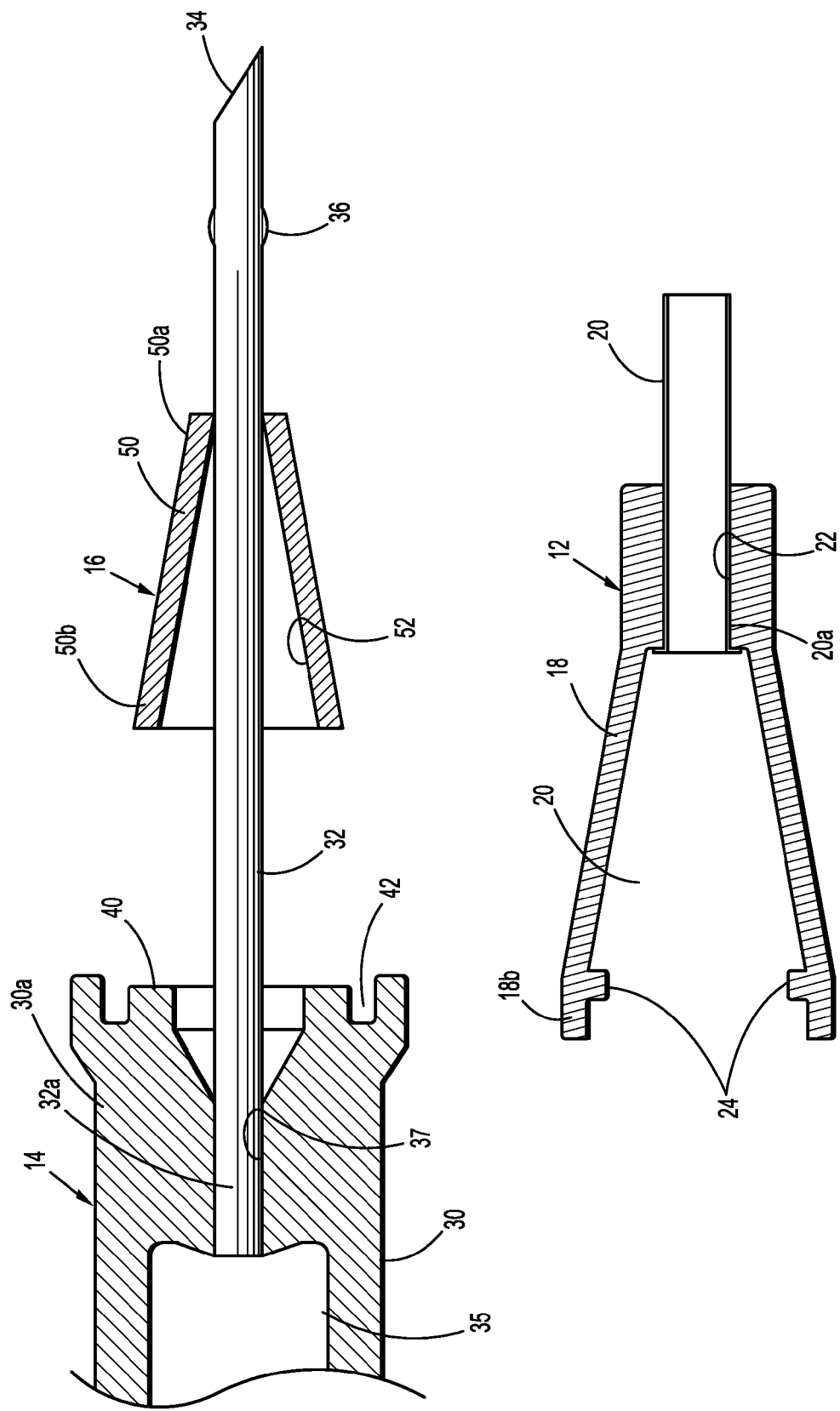
FIG. 2 is a side cross-sectional view with parts separated of the IV catheter and safety needle assembly shown in FIG. 1.

Referring to FIGS. 1 and 2, the presently disclosed IV catheter and safety needle assembly, shown generally as 10, includes a catheter assembly 12, a needle assembly 14 and a needle guard 16 (FIG. 2). Catheter assembly 12 includes a catheter hub 18 and a tubular catheter 20 which is secured to a distal end 18a of the catheter hub 18. Catheter hub 18 defines a receptacle 20 which fluidly communicates with a distal throughbore 22 of catheter hub 18. The proximal end 20a of tubular catheter 20 is secured within the distal throughbore 22 of catheter hub 18 using adhesives, crimping or the like. One or more protrusions 24 are formed on an inner wall of catheter hub 18 which extend into receptacle 20. Alternatively, a single annular protrusion may be provided on the inner wall of catheter hub 18.

Needle assembly 14 includes a needle hub 30 and a hollow needle 32. Needle 32 includes a sharpened distal tip 34 and a distally positioned enlarged diameter portion 36. Enlarged diameter portion 36 is spaced proximally of distal tip 34 and may be formed by crimping the hollow needle 32 or, in the alternative, by applying or forming a protuberance on the needle 32. A proximal end 32a of needle 32 is secured to needle hub 30 using any known fastening technique, e.g., adhesives, crimping, molding or the like. The needle hub 30 defines a chamber 35 which is in fluid communication with a throughbore 37 which extends through the distal end 30a of needle hub 30. Proximal end 32a of needle 32 is secured within throughbore 37 of needle hub 30.

A distal surface 40 of needle hub 30 may define an annular recess 42 which is dimensioned to frictionally receive and engage the proximal end 18b of catheter hub 18. The receipt of needle hub 30 within annular recess 42 releasably secures needle hub 30 to catheter hub 18. In one embodiment, the needle hub 18 is formed from a transparent material such as any polymer including polypropylenes, polycarbonates, polyethylenes or the like, to facilitate visualization of blood flashback within chamber 35.

Needle guard 16 includes a body 50 defining a throughbore 52 having a first diameter at a distal end 50a of body 50 and a second larger diameter at a proximal end 50b of body 50. In one embodiment, the needle guard 16 and the throughbore 52 are conically shaped and the first diameter corresponds to the outer diameter of the needle 32. Alternatively, the needle guard 16 and throughbore 52 may assume any of a variety of different configurations, e.g., a stepped configuration, capable of inversion as will be discussed in further detail below. The first diameter of throughbore 52 is smaller than the outer diameter of enlarged diameter portion 36 of needle 32 as will be discussed in further detail below.

As illustrated in FIG. 3, when the presently disclosed IV catheter and safety needle assembly 10 is assembled, the needle guard 16 is positioned within the receptacle 20 defined by the catheter hub 18 such that the proximal end 50b of needle guard 16 is positioned adjacent to the one or more protrusions 24 formed on the inner wall of catheter hub 18. In addition, proximal end 18b of catheter hub 18 is positioned within the annular recess 42 defined in the distal surface 40 of needle hub 14 to frictionally secure needle hub 14 to catheter hub 18. In this position, the needle 32 of needle assembly 14 extends through receptacle 20 of catheter hub 18 and throughbore 52 of needle guard 16 such that needle tip 34 projects outwardly from tubular catheter 20. Although not shown, a cap or cover may be provided to enclose the needle tip 34 during shipping and storage of the IV catheter and safety needle assembly 10.

Referring to FIG. 4, after tubular catheter 20 has been placed into a patient's vasculature in a known manner by piercing the tissue of a patient with needle tip 34 of needle 32 and proper placement has been confirmed by visualization of blood flashback within chamber 35 of needle hub 30, the needle 32 can be withdrawn from catheter assembly 12 by grasping the catheter hub 18 and pulling needle assembly 14 proximally in relation to catheter assembly 12 in the direction indicated by arrows "A" in FIG. 4. As needle 32 is withdrawn from catheter assembly 12, the needle 32 will pass through the needle guard 16 until the enlarged diameter portion 36 engages the distal end 50a of needle guard 16. Because the enlarged diameter portion 36 of needle 32 is larger in diameter than the inner diameter of throughbore 52 of the distal end 50a of the needle guard 50, further withdrawal of needle 32 from catheter assembly 12 effects movement of the proximal end 50b of needle guard 16 into the one or more protrusions 24 to prevent proximal movement of needle guard 16 in relation to catheter assembly 12.

Referring to FIG. 5, when the proximal end 50b engages the one or more protrusions 24 and the needle 32 is further withdrawn from catheter assembly 12, protrusions 24 cause the needle guard 16 to begin to invert (FIG. 5) such that continued withdrawal of needle 32 from catheter assembly 12 will effect a complete inversion of needle guard 16. Referring to FIG. 6, after the needle guard 16 has been inverted, the needle tip 34 will be enclosed within the inverted needle guard 16. As illustrated, in this position, the enlarged diameter portion 36 of the needle 32 will be in frictional engagement with the smaller diameter end of the throughbore 52 defined by the needle guard 16 to frictionally retain the needle guard 16 on the distal end of needle 32 covering needle tip 34.

Figure 7:
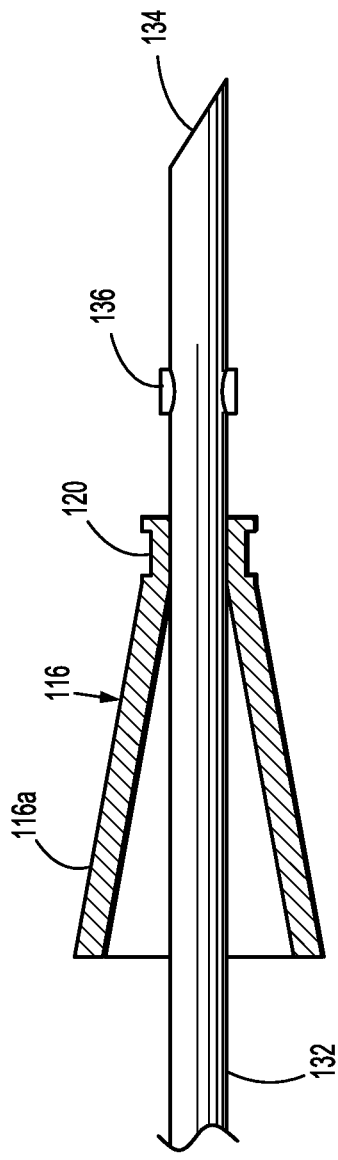
FIG. 7 is side cross-sectional view of an alternate embodiment of the presently disclosed needle and needle guard prior to inversion of the needle guard.
Figure 7A:
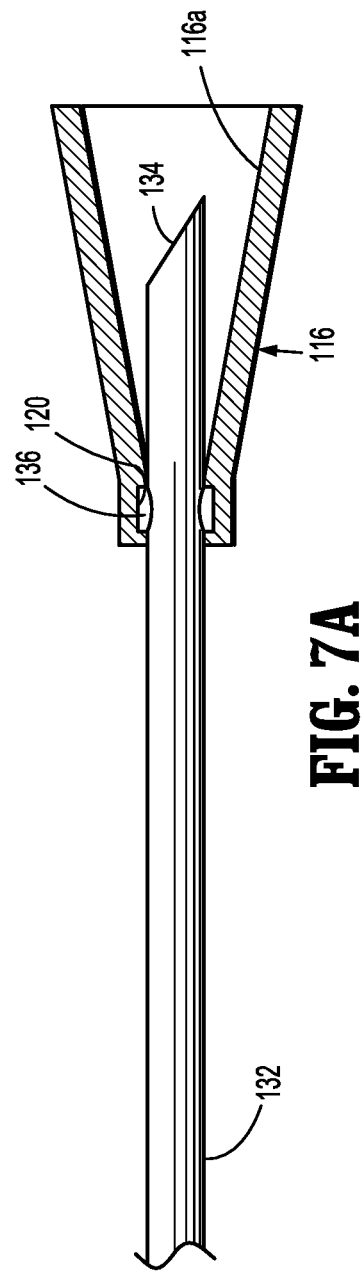
FIG. 7A is a side cross-sectional view of the needle and needle guard shown in FIG. 7 with the needle guard inverted about the needle tip.

Referring to FIGS. 7 and 7A, in an alternative embodiment of the presently disclosed IV catheter and safety needle assembly, the needle guard 116 may include a cutout 120 defined in the outer surface 116a of needle guard 116 which is positioned to receive the enlarged diameter portion 136 of needle 132 when the needle guard 116 is inverted. In addition, the enlarged diameter portion 136 of the needle 132 may include one or more protrusions which are shaped to more effectively secure the needle guard 116 to the needle 132 after the needle guard 116 has been inverted about the needle tip 134. For example, one or both of the ends the protrusions may be substantially vertical to prevent withdrawal of the protrusions 136 from cutout 120 of needle guard 116.

Although the presently disclosed needle assembly and needle guard are described herein in association with an IV catheter assembly, it is envisioned that the needle assembly and needle guard would function properly absent the IV catheter assembly. In such a device, the needle guard 16, 116 would be positioned about needle 32, 132 proximally of enlarged diameter portion 36, 136 during use of the needle 32. After the needle 32, 132 has been used, the needle guard 16, 116 is manually advanced along needle 32, 132 to move the distal end of the needle guard 16, 116 into engagement with the enlarged diameter portion of the needle 32, 132 such that needle guard 16, 116 is inverted about the distal tip 34, 134 of needle 32, 132.

The components of the presently disclosed IV catheter and safety needle assembly may be formed from a variety of different materials as known in the art. For example, the tubular catheter may be fabricated from polyurethanes or silicone, the needle hub and catheter hub may be fabricated from polymers including polyether imides, ABS resins and polyethylene, and the needle may be fabricated from stainless steel, titanium, as well as from polymers. Additionally, other materials of composition are envisioned.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. An IV catheter and safety needle assembly comprising:
a catheter assembly including a catheter hub defining a receptacle and a tubular catheter extending distally from and in fluid communication with the receptacle, the catheter hub including one or more protrusions extending from an inner wall of the catheter hub into the receptacle;
a needle assembly including a needle hub defining a chamber and a needle in fluid communication with the chamber, the needle including a sharpened distal tip and an enlarged diameter portion disposed proximally of the distal tip, the needle being dimensioned to extend through the catheter assembly such that the sharpened tip extends from a distal end of the tubular catheter; and
a needle guard supported within the receptacle and having a proximal end positioned adjacent to the one or more protrusions and a distal end having an inner diameter which is smaller than the enlarged diameter portion of the needle, wherein upon withdrawal of the needle from the catheter assembly, the enlarged diameter portion of the needle is positioned to engage the distal end of the needle guard to move the needle guard into the one or more protrusions and effect an inversion of the needle guard about the sharpened tip of the needle.

2. The IV catheter and safety needle assembly according to claim 1, wherein the enlarged diameter portion of the needle defines a crimp.

3. The IV catheter and safety needle assembly according to claim 1 wherein the enlarged diameter portion of the needle includes a protuberance formed on the needle.

4. The IV catheter and safety needle assembly according to claim 1, wherein the needle guard defines a conical throughbore having a diameter at a proximal end which is larger than the inner diameter at the distal end.

5. The IV catheter and safety needle assembly according to claim 4, wherein the needle guard has a conical configuration.

6. The IV catheter and safety needle assembly according to claim 1, wherein the needle hub defines a flashback chamber.

7. The IV catheter and safety needle assembly according to claim 6, wherein the needle hub is formed from a transparent material.

8. The IV catheter assembly comprising:
a catheter assembly including a catheter hub defining a receptacle and a tubular catheter extending distally from and in fluid communication with the receptacle, the catheter hub including one or more protrusions extending from an inner wall of the catheter hub into the receptacle;
a needle assembly including a needle hub defining a chamber and a needle in fluid communication with the chamber, the needle including a sharpened distal tip and an enlarged diameter portion disposed proximally of the distal tip, the needle being dimensioned to extend through the catheter assembly such that the sharpened tip extends from a distal end of the tubular catheter; and
a needle guard supported within the receptacle and having a proximal end positioned adjacent to the one or more protrusions and a distal end having an inner diameter which is smaller than the enlarged diameter portion of the needle, wherein upon withdrawal of the needle from the catheter assembly, the enlarged diameter portion of the needle is positioned to engage the distal end of the needle guard to move the needle guard into the one or more protrusions and effect an inversion of the needle guard about the sharpened tip of the needle;
wherein the needle guard includes a cutout formed in an outer surface of the needle guard, the cutout being positioned and configured to receive the enlarged diameter portion of the needle upon inversion of the needle guard.

9. The IV catheter and safety needle assembly according to claim 8, wherein the enlarged diameter portion of the needle is configured to resist removal of the enlarged diameter portion from the cutout.

10. The IV catheter and safety needle assembly according to claim 1, wherein the enlarged diameter portion of the needle is dimensioned to frictionally engage the inner diameter of the needle guard after inversion of the needle to retain the needle guard on the tip of the needle.

11. The IV catheter and safety needle assembly according to claim 8, wherein the enlarged diameter portion of the needle defines a crimp.

12. The IV catheter and safety needle assembly according to claim 8 wherein the enlarged diameter portion of the needle includes a protuberance formed on the needle.

13. The IV catheter and safety needle assembly according to claim 8, wherein the needle guard defines a conical throughbore having a diameter at a proximal end which is larger than the inner diameter at the distal end.

14. The IV catheter and safety needle assembly according to claim 13, wherein the needle guard has a conical configuration.

15. The IV catheter and safety needle assembly according to claim 8, wherein the needle hub defines a flashback chamber.

16. The IV catheter and safety needle assembly according to claim 15, wherein the needle hub is formed from a transparent material.

17. The IV catheter and safety needle assembly according to claim 8, wherein the enlarged diameter portion of the needle is dimensioned to frictionally engage the inner diameter of the needle guard after inversion of the needle to retain the needle guard on the tip of the needle.

* * * * *